(12) United States Patent
Akama et al.

(10) Patent No.: US 6,869,971 B1
(45) Date of Patent: Mar. 22, 2005

(54) UCS1025 DERIVATIVES

(75) Inventors: Tsutomu Akama, Sunnyvale, CA (US); Akira Asai, San Diego, CA (US); Tsutomu Agatsuma, Machida (JP); Shinji Nara, Sunto-gun (JP); Yoshinori Yamashita, Sunto-gun (JP); Tamio Mizukami, Chiyoda-Ku (JP); Shun-ichi Ikeda, Machida (JP); Yutaka Saitoh, Sunto-gun (JP); Yutaka Kanda, Sunto-gun (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/110,964

(22) PCT Filed: Oct. 19, 2000

(86) PCT No.: PCT/JP00/07287
§ 371 (c)(1),
(2), (4) Date: Apr. 18, 2002

(87) PCT Pub. No.: WO01/29043
PCT Pub. Date: Apr. 26, 2001

(30) Foreign Application Priority Data

Oct. 21, 1999 (JP) ............................................ 11/298972

(51) Int. Cl.[7] .................. A61K 31/403; A61K 31/4453; C07D 209/52; C07D 401/06
(52) U.S. Cl. ........................ 514/413; 514/323; 548/453; 546/201
(58) Field of Search .......................... 548/453; 514/413, 514/323; 546/201

(56) References Cited

U.S. PATENT DOCUMENTS 5,798,379 A    8/1998   Mizukami et al. .......... 514/441

FOREIGN PATENT DOCUMENTS

EP    0 849 267    6/1998
JP    09-227514    9/1997

OTHER PUBLICATIONS

Lala et al., Role of nitric oxide in tumor progression: Lessons from experimental tumors, Cancer and Metastasis Reviews, Kluwer Academic Publishers, 1998 17(1), 91–106.*

West, et al., "ZG–1494α, a Novel Platelet–activating Factor Acetyltransferase . . . ", The Journal of Antibiotics, vol. 49, No. 10, pp. 967–973 (1996).

Singh, et al., "Oteromycin: A Novel Antagonist of Endothelin Receptor", J. Org. Chem., vol. 60 (1995), pp. 7040–7042.

Grote, et al., "Pyrrolams, New Pyrrolizidinones Produced . . . ", Metabolic Products of Microorganisms, vol. 256 (1989), pp. 525–530.

Flitsch, et al., "Pyrrolizidin–Synthesen, II", Liebigs Ann. Chem., (1988), pp. 381–385.

* cited by examiner

Primary Examiner—Joseph K. McKane
Assistant Examiner—Rebecca Anderson
(74) Attorney, Agent, or Firm—Fitzpatrick, Cella, Harper & Scinto

(57) ABSTRACT

UCS 1025 derivatives having antitumor activity or antibacterial activity which are represented by formula (I):

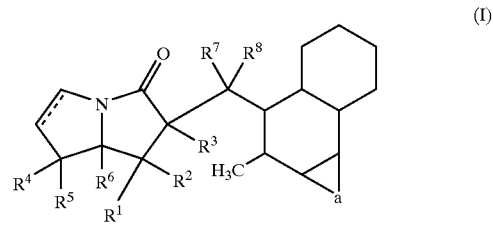

(I)

wherein $R^1$ represents hydrogen, lower alkyl, etc.; $R^2$ represents hydrogen, or is combined with $R^3$ to represent a bond, etc., or is combined with $R^4$ to represent —O(C=O)—, etc.; $R^3$ represents hydrogen, etc., or is combined with $R^2$ to represent a bond, etc.; $R^4$ represents hydrogen, etc., or is combined with $R^2$ to represent —(C=O)O—, etc.; $R^5$ represents hydrogen or is combined with $R^6$ to represent a bond; $R^6$ represents hydrogen, etc., or is combined with $R^5$ to represent a bond; $R^7$ represents hydrogen or is combined with $R^8$ to represent =O; $R^8$ represents hydroxy or is combined with $R^7$ to represent =O; ---- represents a single bond or a double bond, and a represents a single bond (two carbon atoms to which a is bound are combined to form a single bond) or an oxygen atom, or pharmaceutically acceptable salts thereof.

13 Claims, No Drawings

UCS1025 DERIVATIVES

TECHNICAL FIELD

The present invention relates to UCS 1025 derivatives having antitumor activity or antibacterial activity.

BACKGROUND ART

Examples of known compounds in which the 1-position of a decalin ring and the 3-position of 2-pyrrolidone are bound via carbonyl include ZG-1494α having a platelet-activating factor acetyltransferase inhibitory activity which is represented by formula (II):

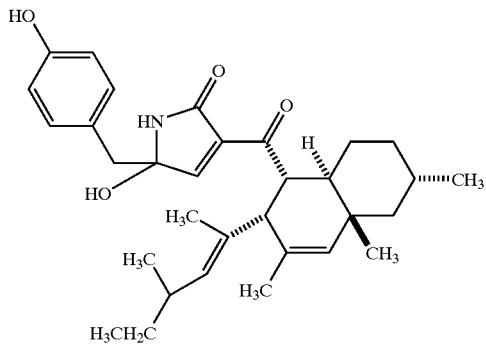

(II)

(J. Antibiotics, 49, 967–973 (1996)), oteromycin having an endothelin receptor antagonistic activity which is represented by formula (III):

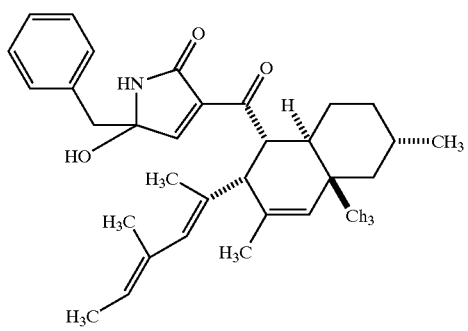

(III)

(J. Org. Chem., 60, 7040–7042 (1995)) and the like.

Examples of known compounds having a pyrrolizidinone skeleton include pyrrolam A represented by formula (IV):

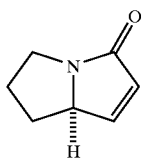

(IV)

(Liebig. Ann. Chem., 525–530 (1990)), compounds represented by formulae (V) to (VIII)

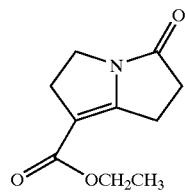

(V)

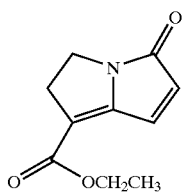

(VI)

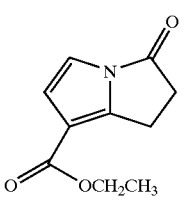

(VII)

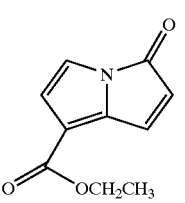

(VIII)

(Liebig. Ann. Chem., 381–385 (1988)) and the like, but antibacterial and antitumor activities are not known in each of the above-mentioned compounds.

As a compound having antibacterial activity, F-12434 represented by formula (IX):

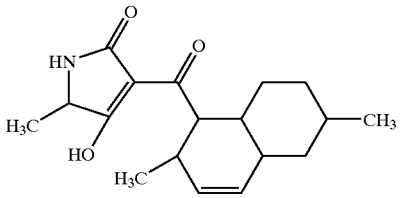

(IX)

is known (Japanese Published Unexamined Patent Application No. 227514/97), and, as compounds having antibacterial activity and antitumor activity, UCS 1025A represented by formula (X) wherein R is hydrogen and UCS 1025B represented by formula (X) wherein R is hydroxy:

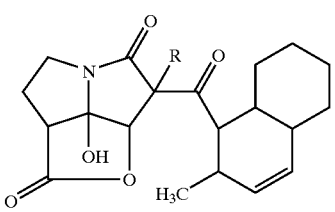

(X)

are known (Japanese Published Unexamined Patent Application No. 245385/98).

DISCLOSURE OF THE INVENTION

An object of the present invention is to provide novel UCS 1025 derivatives having excellent antitumor activity or antibacterial activity.

The present invention relates to UCS 1025 derivatives represented by formula (I):

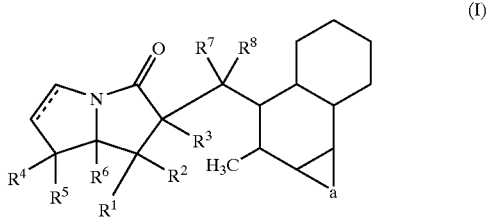

(I)

wherein $R^1$ represents hydrogen, lower alkyl, $NR^9R^{10}$ (wherein $R^9$ and $R^{10}$ are the same or different and each represents hydrogen, substituted or unsubstituted lower alkyl, substituted or unsubstituted lower alkenyl, substituted or unsubstituted lower alkynyl, substituted or unsubstituted aryl, substituted or unsubstituted aralkyl or $OR^{11}$ (wherein $R^{11}$ represents hydrogen or lower alkyl), or $R^9$ and $R^{10}$ are combined together with the adjacent N to form a substituted or unsubstituted heterocyclic ring), $SR^{12}$ (wherein $R^{12}$ represents hydrogen, substituted or unsubstituted lower alkyl, substituted or unsubstituted lower alkenyl, substituted or unsubstituted lower alkynyl, substituted or unsubstituted aryl, or substituted or unsubstituted aralkyl) or $OR^{13}$ (wherein $R^{13}$ represents hydrogen, substituted or unsubstituted lower alkyl, substituted or unsubstituted lower alkenyl, or substituted or unsubstituted lower alkynyl), $R^2$ represents hydrogen, is combined with $R^3$ to represent a bond, —O— or —CH=N—NH— ($R^2$ binds at the CH side of —CH=N—NH— and $R^3$ binds at the NH side of —CH=N—NH—, respectively), or is combined with $R^4$ to represent —O(C=O)—($R^2$ binds at the O side of —O(C=O)— and $R^4$ binds at the (C=O) side of —O(C=O)—, respectively) or —$NR^{14}$(C=O)— ($R^2$ binds at the $NR^{14}$ side of —$NR^{14}$(C=O)— and $R^4$ binds at the (C=O) side of —$NR^{14}$(C=O)—, respectively; and $R^{14}$ represents hydrogen, substituted or unsubstituted lower alkyl, substituted or unsubstituted lower alkenyl, substituted or unsubstituted lower alkynyl, substituted or unsubstituted aryl, or substituted or unsubstituted aralkyl), $R^3$ represents hydrogen, $OR^{15}$ (wherein $R^{15}$ represents hydrogen, substituted or unsubstituted lower alkyl, substituted or unsubstituted lower alkenyl, substituted or unsubstituted lower alkynyl, substituted or unsubstituted aralkyl, or substituted or unsubstituted lower alkanoyl) or halogen, or is combined with $R^2$ to represent a bond, —O— or —NH—N=CH— ($R^3$ binds at the NH side of —NH—N=CH— and $R^2$ binds at the CH side of —NH—N=CH—, respectively), $R^4$ represents hydrogen, $CO_2R^{16}$ (wherein $R^{16}$ represents hydrogen, substituted or unsubstituted lower alkyl, substituted or unsubstituted lower alkenyl, substituted or unsubstituted lower alkynyl, substituted or unsubstituted aryl, or substituted or unsubstituted aralkyl) or $CONR^{17}R^{18}$ (wherein $R^{17}$ and $R^{18}$ are the same or different and each represents hydrogen, substituted or unsubstituted lower alkyl, substituted or unsubstituted lower alkenyl, substituted or unsubstituted lower alkynyl, substituted or unsubstituted aryl, or substituted or unsubstituted aralkyl, or $R^{17}$ and $R^{18}$ are combined together with the adjacent N to form a substituted or unsubstituted heterocyclic ring), or is combined with $R^2$ to represent —(C=O)O— ($R^4$ binds at the (C=O) side of —(C=O)O— and $R^2$ binds at the O side of —(C=O)O—, respectively) or —(C=O)$NR^{14}$— ($R^4$ binds at the (C=O) side of —(C=O)$NR^{14}$— and $R^2$ binds at the $NR^{14}$ side of —(C=O)$NR^{14}$—, respectively; and $R^{14}$ has the same meaning as defined above), $R^5$ represents hydrogen or is combined with $R^6$ to represent a bond, $R^6$ represents hydrogen or $OR^{19}$ (wherein $R^{19}$ has the same meaning as the above $R^{15}$), or is combined with $R^5$ to represent a bond, $R^7$ represents hydrogen or is combined with $R^8$ to represent =O, $R^8$ represents hydroxy or is combined with $R^7$ to represent =O, ---- represents a single bond or a double bond, and a represents a single bond (two carbon atoms to which a is bound are combined to form a single bond to thereby form a double bond) or an oxygen atom, with the proviso that 1) a compound in which $R^2$ and $R^4$ are combined to represent —O(C=O)—, $R^1$ represents hydrogen, $R^3$ represents hydrogen or hydroxy, $R^1$ represents hydrogen, $R^6$ represents hydroxy, $R^7$ and $R^8$ are combined to represent =O, and ---- and a represent a single bond, and 2) a compound in which $R^1$ represents hydrogen, $R^2$ and $R^3$ are combined to represent a bond, $R^4$ represents carboxy, $R^5$ represents hydrogen, $R^6$ represents hydroxy, $R^7$ and $R^8$ are combined to represent =O, and ---- and a represent a single bond are excluded, or pharmaceutically acceptable salts thereof.

The present invention relates to UCS 1025 derivatives, wherein, in formula (I), $R^4$ is hydrogen, $CO_2R^{16}$ (wherein $R^{16}$ has the same meaning as defined above) or $CONR^{17}R^{18}$ (wherein $R^{17}$ and $R^{18}$ have the same meanings as defined above), or pharmaceutically acceptable salts thereof.

The present invention relates to UCS 1025 derivatives, wherein, in formula (I), $R^1$ is hydrogen, $NR^9R^{10}$ (wherein $R^9$ and $R^{10}$ have the same meanings as defined above), $SR^{12}$ (wherein $R^{12}$ has the same meaning as defined above) or $OR^{13}$ (wherein $R^{13}$ has the same meaning as defined above), or pharmaceutically acceptable salts thereof.

The present invention relates to UCS 1025 derivatives, wherein, in formula (I), $R^2$ and $R^3$ represent hydrogen at the same time or $R^2$ and $R^3$ are combined to represent a bond, or pharmaceutically acceptable salts thereof. Among these, preferred examples include UCS 1025 derivatives, wherein $R^4$ is hydrogen, $CO_2R^{16}$ (wherein $R^{16}$ has the same meaning as defined above) or $CONR^{17}R^{18}$ (wherein $R^{17}$ and $R^{18}$ have the same meanings as defined above), or pharmaceutically acceptable salts; and UCS 1025 derivatives, wherein $R^1$ is hydrogen, $NR^9R^{10}$ (wherein $R^9$ and $R^{10}$ have the same meanings as defined above), $SR^{12}$ (wherein $R^{12}$ has the same meaning as defined above) or $OR^{13}$ (wherein $R^{13}$ has the same meaning as defined above), or pharmaceutically acceptable salts thereof.

The present invention relates to UCS 1025 derivatives, wherein, in formula (I), $R^7$ and $R^8$ are combined to represent =O, or pharmaceutically acceptable salts thereof. Among these, preferred examples include UCS 1025 derivatives, wherein $R^4$ is hydrogen, $CO_2R^{16}$ (wherein $R^{16}$ has the same meaning as defined above) or $CONR^{17}R^{10}$ (wherein $R^{17}$ and $R^{18}$ have the same meanings as defined above), or pharmaceutically acceptable salts thereof; UCS 1025 derivatives, wherein $R^1$ is hydrogen, $NR^9R^{10}$ (wherein $R^9$ and $R^{10}$ have the same meanings as defined above), $SR^{12}$ (wherein $R^{12}$ has the same meaning as defined above) or $OR^{13}$ (wherein $R^{13}$ has the same meaning as defined above), or pharmaceutically acceptable salts thereof; and UCS 1025 derivatives, wherein $R^2$ and $R^3$ represent hydrogen at the same time or $R^2$ and $R^3$ are combined to represent a bond, or pharmaceutically acceptable salts thereof.

The present invention relates to an antibacterial agent comprising, as an active ingredient, the UCS 1025 derivative represented by formula (I) or a pharmaceutically acceptable salt thereof.

The present invention relates to an antitumor agent comprising, as an active ingredient, the UCS 1025 derivative represented by formula (I) or a pharmaceutically acceptable salt thereof.

The present invention relates to a medicament comprising, as an active ingredient, the UCS 1025 derivative represented by formula (I) or a pharmaceutically acceptable salt thereof.

The present invention relates to a method for treating malignant tumors, which comprises administering a therapeutically effective amount of the UCS 1025 derivative represented by formula (I) or a pharmaceutically acceptable salt thereof.

The present invention relates to use of the UCS 1025 derivative represented by formula (I) or a pharmaceutically acceptable salt thereof for manufacturing an antitumor agent.

Hereinafter, the compound represented by formula (I) is called Compound (I), and the same applies to the compounds of other formula numbers.

In the definition of each group of formula (I), the lower alkyl includes straight or branched alkyl having 1 to 6 carbon atoms, such as methyl, ethyl, propyl, isopropyl, butyl, isobutyl, pentyl, hexyl and the like. The lower alkanoyl includes straight or branched alkanoyl having 1 to 6 carbon atoms, such as formyl, acetyl, propionyl, butyryl, isobutyryl, pentanoyl, hexanoyl and the like. The lower alkenyl includes alkenyl having 2 to 6 carbon atoms, such as vinyl, allyl, butenyl, pentenyl, hexenyl and the like, and the lower alkynyl includes alkynyl having 2 to 6 carbon atoms, such as ethynyl, propynyl, butynyl, pentynyl, hexynyl and the like. The halogen means each atom of iodine, bromine, chlorine or fluorine. Examples of the aryl include phenyl, naphthyl, pyridyl, thienyl, furyl, pyrrolyl, imidazolyl, pyrimidinyl, oxazolyl, thiazolyl and the like. Examples of the heterocyclic ring formed together with the adjacent N include pyrrolidinyl, piperidino, piperazinyl, morpholino, thiomorpholino, pyrrolyl, imidazolyl, pyrazolyl and the like. The aryl moiety of the aralkyl has the same meaning as the above aryl, and the alkylene moiety of the aralkyl means a group in which one hydrogen atom is removed from the above lower alkyl.

Examples of the substituent in the substituted lower alkyl, the substituted lower alkenyl, the substituted lower alkynyl, the substituted lower alkanoyl, the substituted aryl and the substituted aralkyl include 1 to substitutable number of, preferably 1 to 3, substituents which are the same or different, such as $NR^{20}R^{21}$ (wherein $R^{20}$ and $R^{21}$ are the same or different and each represents hydrogen, lower alkyl, aryl or aralkyl, or $R^{20}$ and $R^{21}$ are combined together with the adjacent N to form a heterocyclic ring), nitro, carboxy, $CONR^{22}R^{23}$ (wherein $R^{22}$ and $R^{23}$ are the same or different and each represents hydrogen, lower alkyl, lower alkenyl, lower alkynyl, lower alkanoyl, aryl or aralkyl), cyano, halogen, hydroxy, lower alkoxy, lower alkoxycarbonyl, lower alkylthio, lower alkanoyl, lower alkanoyloxy, aryl, aralkyl and the like. The lower alkyl, the lower alkenyl, the lower alkynyl, the lower alkanoyl, the aryl, the aralkyl, the heterocyclic ring formed together with the adjacent N, and the halogen have the same meanings as defined above, respectively. The lower alkyl moieties of the lower alkoxy, the lower alkoxycarbonyl and the lower alkylthio have the same meaning as the above lower alkyl. The lower alkanoyl moiety of the lower alkanoyloxy has the same meaning as the above lower alkanoyl.

Examples of the substituent in the substituted heterocyclic ring include aralkyloxy in addition to those exemplified as the substituent of the substituted lower alkyl, the substituted lower alkenyl, the substituted lower alkynyl, the substituted lower alkanoyl and the substituted aralkyl. The aryl moiety and the alkylene moiety of aralkyl in the aralkyloxy have the same meanings as defined above, respectively.

Examples of the pharmaceutically acceptable salts of Compound (I) include pharmaceutically acceptable acid addition salts, metal addition salts, base addition salts and the like. Examples of the pharmaceutically acceptable acid addition salts include inorganic acid salts such as hydrochloride, hydrobromide, sulfate, phosphate and the like; organic acid salts such as methanesulfonate, oxalate, acetate, malonate, succinate, fumarate, maleate, tartrate, citrate and the like; and amino acid addition salts such as lysine salt, glycine salt, phenylalanine salt and the like. Examples of the pharmaceutically acceptable metal addition salts include alkali metal salts such as sodium salt, potassium salt and the like; alkaline earth metal salts such as magnesium salt, calcium salt and the like; aluminum salt; zinc salt; and the like. Examples of the pharmaceutically acceptable base addition salts include ammonium salts such as ammonium, tetramethylammonium and the like; and addition salts of an organic amine such as morpholine, piperidine or the like.

Some Compounds (I) of the present invention include may exist in variety form of an isomer such as a stereoisomer, a regio isomer, a geometrical isomer, a tautomer or the like. All of these possible isomers and mixtures thereof are included in the present invention, and the mixing ratio may be any optional ratio.

Next, production methods of Compound (I) are described.

When defined groups are changed under conditions of each method or unsuitable for carrying out the method in the production methods shown below, the production can be easily carried out by employing methods generally used in the synthetic organic chemistry, such as protection and deprotection of functional groups (e.g., see *Protective Groups in Organic Synthesis*, edited by T. W. Greene, John Wiley & Sons, Inc. (1981) and the like). Also, the order of the reaction steps such as an introduction of the substituent and the like can be changed if necessary.

Production Method 1

Compound (Ia) which is Compound (I) wherein $R^4$ represents $CO_2R^{16a}$ (wherein $R^{16a}$ represents substituted or unsubstituted lower alkyl, substituted or unsubstituted lower alkenyl, substituted or unsubstituted lower alkynyl, or substituted or unsubstituted aralkyl) can be produced by the following reaction step.

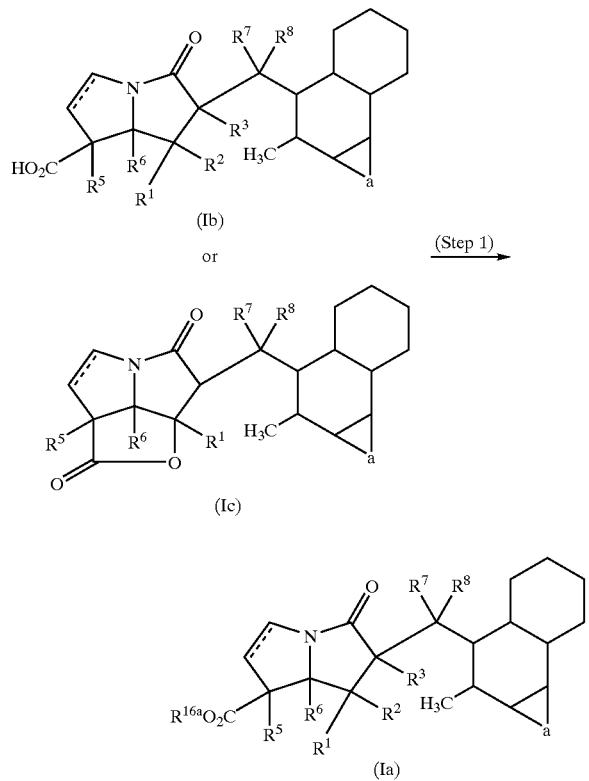

(wherein $R^1$, $R^2$, $R^3$, $R^4$, $R^5$, $R^6$, $R^7$, $R^8$, $R^{16a}$, a and ---- have the same meanings as defined above, respectively).

Step 1:

Compound (Ia) can be produced by reacting Compound (Ib) which is Compound (I) wherein $R^4$ represents carboxy, or Compound (Ic) which is Compound (I) wherein $R^2$ and $R^4$ are combined to represent —O(C=O)— and $R^3$ represents hydrogen with a halide represented by $R^{16a}X$ (wherein $R^{16a}$ has the same meaning as defined above; and X represents chlorine, bromine or iodine) in an inert solvent in the presence of an appropriate base.

The inert solvent includes ethers such as tetrahydrofuran, dioxane, etc., dimethylformamide, dichloromethane and the like. The base includes sodium carbonate, sodium bicarbonate, potassium carbonate, sodium hydroxide, potassium hydroxide, sodium hydride, potassium tert-butoxide, diisopropylethylamine, 1,4-diazabicyclo[2,2,2]octane, 1,8-diazabicyclo[5,4,0]-7-undecene and the like, which are used in an amount of 1 to 30 equivalents based on Compound (Ib) or Compound (Ic).

The halide represented by $R^{16a}X$ (wherein $R^{16a}$ and X have the same meanings as defined above, respectively) is used in an amount of 1 to 30 equivalents based on Compound (Ib) or Compound (Ic), and if necessary, sodium iodide or potassium iodide may be added in an amount of 1 to 30 equivalents. The reaction is completed at 0° C. to the boiling point of the used solvent, preferably at 20 to 30° C., in 1 to 48 hours.

Compound (Ia) can also be obtained by the following method. That is, it can be produced by reacting Compound (Ib) or Compound (Ic) with 1 to 100 equivalents of a compound represented by $HOR^{16a}$ (wherein $R^{16a}$ has the same meaning as defined above) in an inert solvent in the presence of a condensing agent.

The inert solvent is the same as the above case, and the condensing agent is not particularly limited, so long as it can be applied to the condensation of a carboxylic acid and an alcohol. Examples thereof include 1-(3-dimethylaminopropyl)-3-ethylcarbodiimide hydrochloride, dicyclohexylcarbodiimide, 2-chloro-1-methylpyridinium iodide, carbonyldiimidazole, ethyl chloroformate and the like. If necessary, the reaction can be accelerated by adding 1 to 10 equivalents of a base such as 4-dimethylaminopyridine, diisopropylethylamine, triethylamine, pyridine or the like. The reaction is completed at 0° C. to the boiling point of the used solvent, preferably at 20 to 30° C., generally in 0.5 to 72 hours.

When Compound (Ic) is used as the starting material in the above production method, a compound which is Compound (Ia) wherein $R^2$ and $R^3$ are combined to form a bond is obtained.

Production Method 2

Compound (Id) which is Compound (I) wherein $R^4$ represents $CONR^{17}R^{18}$ (wherein $R^{17}$ and $R^{18}$ have the same meanings as defined above, respectively), or Compound (Ie) which is Compound (I) wherein $R^2$ and $R^4$ are combined to represent —$NR^{14}$(C=O)— (wherein $R^{14}$ has the same meaning as defined above) can be produced by the following reaction steps.

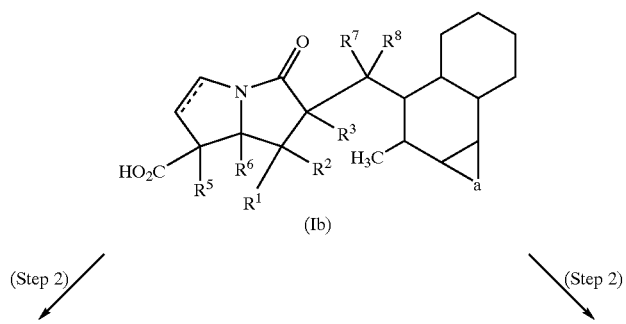

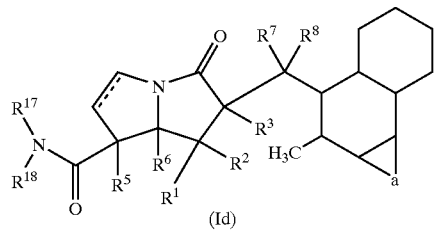

(Id)

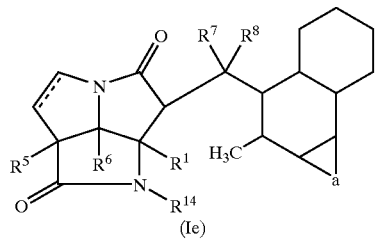

(Ie)

(Step 2)　　　　　　　　　　(Step 2)

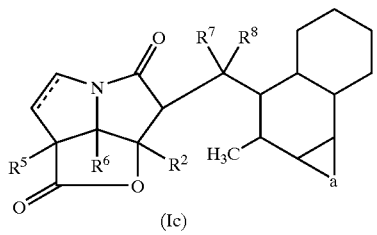

(Ic)

(wherein $R^1$, $R^2$, $R^3$, $R^5$, $R^6$, $R^7$, $R^8$, $R^{14}$, $R^{17}$, $R^{18}$, a and ---- having the same meanings as defined above, respectively).

Step 2:

Compound (Id) or Compound (Ie) can be produced by reacting Compound (Ib) which is Compound (I) wherein $R^4$ represents carboxy with 1 to 10 equivalents of an amine represented by $HNR^{17}R^{18}$ (wherein $R^{17}$ and $R^{18}$ have the same meanings as defined above, respectively) or an amine represented by $H_2NR^{14}$ (wherein $R^{14}$ has the same meaning as defined above) in an inert solvent in the presence of an appropriate condensing agent.

Examples of the inert solvent include solvents similar to those described in the Production Method 1. The condensing agent is not particularly limited, so long as it can be applied to the condensation of a carboxylic acid and an amine. Examples thereof include 1-(3-dimethylaminopropyl)-3-ethylcarbodiimide hydrochloride, dicyclohexylcarbodiimide, 2-chloro-1-methylpyridinium iodide, carbonyldiimidazole, ethyl chloroformate and the like. If necessary, the reaction can be accelerated by adding 1 to 10 equivalents of a base such as 4-dimethylaminopyridine, diisopropylethylamine, triethylamine, pyridine or the like. The reaction is completed at 0C to the boiling point of the used solvent, preferably at 20 to 30° C., generally in 0.5 to 72 hours.

Compound (Id) or Compound (Ie) can also be produced by using Compound (Ic) which is Compound (I) wherein $R^2$ and $R^4$ are combined to represent —O(C=O)— and $R^3$ represents hydrogen, as the starting material instead of Compound (Ib), and reacting it with 1 to 10 equivalents of an amine represented by $HNR^{17}R^{18}$ (wherein $R^{17}$ and $R^{18}$ have the same meanings as defined above, respectively) or an amine represented by $H_2NR^{14}$ (wherein $R^{14}$ has the same meaning as defined above) in an inert solvent in the presence of an appropriate condensing agent.

Examples of the inert solvent include solvents similar to those described in the Production Method 1. Examples of the appropriate condensing agent include agents similar to those used in the production of Compound (Id) or Compound (Ie) from Compound (Ib). If necessary, as in the case of the production of Compound (Id) or Compound (Ie) from Compound (Ib), the reaction can be accelerated by adding 1 to 10 equivalents of a base such as 4-dimethylaminopyridine, diisopropylethylamine, triethylamine, pyridine or the like. Also, the reaction temperature and reaction time are similar to those in the production of Compound (Id) or Compound (Ie) from Compound (Ib).

When Compound (Ic) is used as the starting material, a compound which is Compound (Id) wherein $R^2$ and $R^3$ are combined to form a bond is obtained.

Production Method 3

Compound (Ifa) which is Compound (I) wherein ---- represents a single bond and $R^5$ and $R^6$ are combined to represent a bond and Compound (Ifb) which is Compound (I) wherein ---- represents a double bond and $R^5$ and $R^6$ are combined to represent a bond can be produced by the following reaction step.

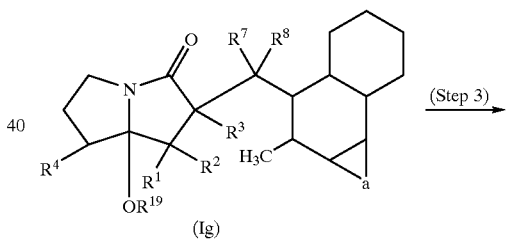

(Ig)

(Step 3)

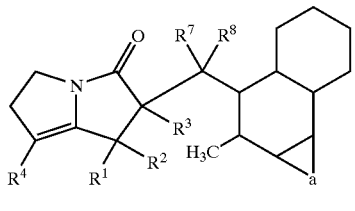

(Ifa)

and

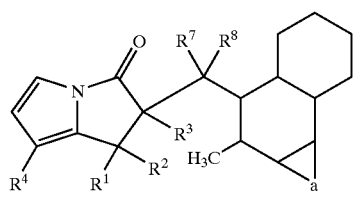

(Ifb)

(wherein $R^1$, $R^2$, $R^3$, $R^4$, $R^7$, $R^8$, $R^{19}$ and a have the same meanings as defined above, respectively).

Step 3:

Compound (Ifa) and Compound (Ifb) can be obtained by treating Compound (Ig) which is Compound (I) wherein ---- represents a single bond, $R^5$ represents hydrogen and $R^6$ represents $OR^{19}$ (wherein $R^{19}$ has the same meaning as defined above) with an appropriate acid catalyst in an inert solvent.

The inert solvent includes hydrocarbons such as toluene, hexane, etc.; ethers such as tetrahydrofuran, dioxane, etc.; dichloromethane; chloroform; and the like. The appropriate acid catalyst includes protic acids such as p-toluenesulfonic acid, pyridinium p-toluenesulfonate, hydrogen chloride, hydrogen bromide, acetic acid, trifluoroacetic acid and the like, and Lewis acids such as aluminum chloride, a boron trifluoride ether complex, titanium tetrachloride and the like, which are used in an amount of 0.1 to 10 equivalents. The reaction is completed at 0° C. to the boiling point of the used solvent generally in 0.1 to 10 hours.

Production Method 4

Compound (Ih) which is Compound (I) wherein $R^3$ is chlorine, bromine or iodine can be produced by the following reaction step.

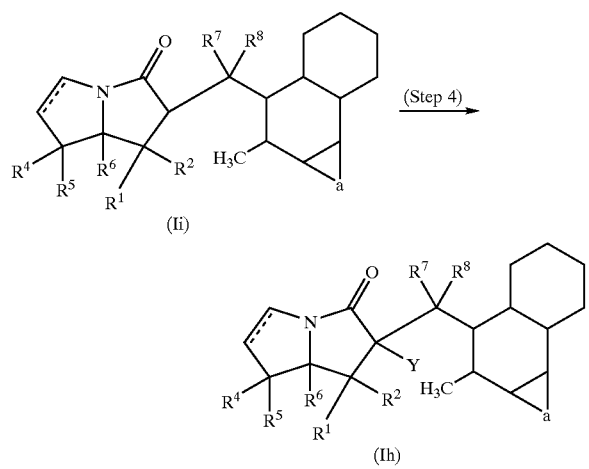

(wherein $R^1$, $R^2$, $R^4$, $R^5$, $R^6$, $R^7$, $R^8$, a and ---- have the same meanings as defined above, respectively; and Y represents chlorine, bromine or iodine).

Step 4:

Compound (Ih) can be obtained by reacting Compound (Ii) which is Compound (I) wherein $R^3$ represents hydrogen with 1 to 10 equivalents of N-chlorosuccinimide, N-bromosuccinimide, N-iodosuccinimide or the like in an inert solvent such as tetrahydrofuran, dioxane, dimethylformamide, dichloromethane or the like. The reaction is completed at 0° C. to the boiling point of the used solvent, preferably at 20 to 80° C., generally in 0.5 to 10 hours.

Production Method 5

Compound (Ij) which is Compound (I) wherein $R^2$ and $R^3$ are combined to represent a bond can be produced by the following reaction step.

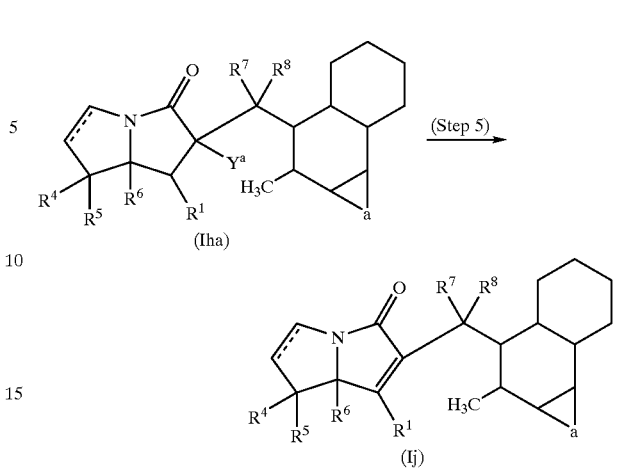

(wherein $R^1$, $R^4$, $R^5$, $R^6$, $R^7$, $R^8$, a and ---- have the same meanings as defined above, respectively; and $Y^a$ represents bromine or iodine).

Step 5:

Compound (Ij) can be obtained by treating Compound (Iha) which is Compound (I) wherein $R^2$ represents hydrogen and $Y^a$ represents bromine or iodine with 1 to 10 equivalents of a base such as potassium tert-butoxide, diisopropylethylamine, 4-dimethylaminopyridine, 1,4-diazabicyclo[2,2,2]octane, 1,8-diazabicyclo[5,4,0]-7-undecene or the like in an inert solvent such as tetrahydrofuran, dioxane, dimethylformamide, dichloromethane or the like. The reaction is completed at −20° C. to the boiling point of the used solvent, preferably at 0 to 30° C., generally in 0.5 to 10 hours.

Production Method 6

Compound (Ika) which is Compound (I) wherein $R^1$ is $NR^9R^{10}$ (wherein $R^9$ and $R^{10}$ have the same meanings as defined above, respectively) or $SR^{12}$ (wherein $R^{12}$ has the same meaning as defined above) can be produced by the following reaction step.

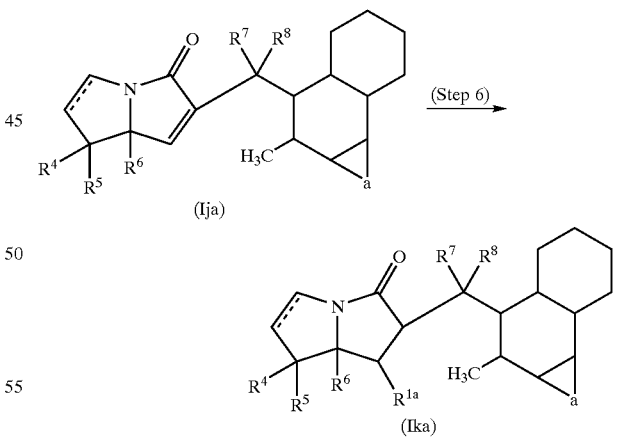

{wherein $R^4$, $R^5$, $R^6$, $R^7$, $R^8$, a and ---- have the same meanings as defined above, respectively; and $R^{1a}$ represents $NR^9R^{10}$ (wherein $R^9$ and $R^{10}$ have the same meanings as defined above, respectively) or $SR^{12}$ (wherein $R^{12}$ has the same meaning as defined above)}.

Step 6:

Compound (Ika) can be obtained by reacting Compound (Ija) which is Compound (I) wherein $R^2$ and $R^3$ are combined to represent a bond and $R^1$ represents hydrogen with 1 to 10 equivalents of an amine represented by $HNR^9R^{10}$ (wherein $R^9$ and $R^{10}$ have the same meanings as defined above, respectively) or a thiol represented by $HSR^{12}$ (wherein $R^{12}$ has the same meaning as defined above) in an inert solvent, if necessary, in the presence of a base.

The inert solvent includes organic solvents such as dimethyl sulfoxide, dimethylformamide, tetrahydrofuran, dioxane, etc., a phosphate buffer having a pH value of 6 to 10, preferably 7 to 8, and the like, which are used alone or as a mixture. The base is preferably 1 to 10 equivalents of an tertiary amine such as pyridine, 4-dimethylaminopyridine, triethylamine, diisopropylethylamine or the like. The reaction is completed at 0° C. to the boiling point of the used solvent, preferably at 20 to 30° C., generally in 0.1 to 10 hours.

Production Method 7

Compound (Im) which is Compound (I) wherein a is an oxygen atom can be produced by the following reaction step.

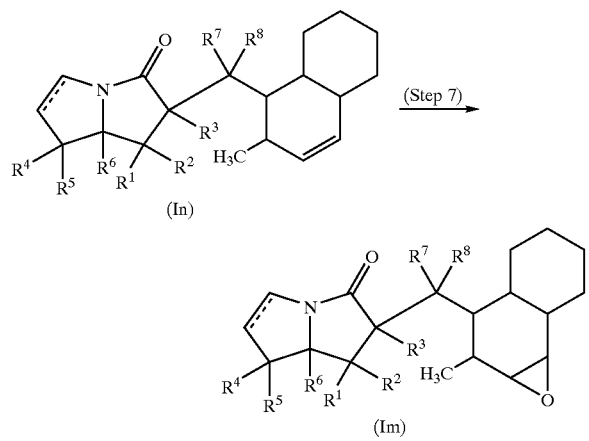

(wherein $R^1$, $R^2$, $R^3$, $R^4$, $R^5$, $R^6$, $R^7$, $R^8$ and ---- have the same meanings as defined above, respectively).

Step 7:

Compound (In) can be obtained by treating Compound (In) which is Compound (I) wherein a represents a single bond with 1 to 10 equivalents of an oxidizing agent in an inert solvent.

The inert solvent includes dichloromethane, chloroform, methanol, ethanol and the like, which are used alone or as a mixture. The oxidizing agent is preferably m-chloroperbenzoic acid, dimethyldioxirane or the like. The reaction is completed at 0° C. to the boiling point of the used solvent, preferably at 20 to 30° C., generally in 0.5 to 24 hours.

Production Method 8

Compound (Ip) which is Compound (I) wherein $R^3$ and/or $R^6$ represents $OR^{15a}$ (wherein $R^{15a}$ represents substituted or unsubstituted lower alkyl, substituted or unsubstituted lower alkenyl, substituted or unsubstituted lower alkynyl, or substituted or unsubstituted aralkyl) can be produced by the following reaction step.

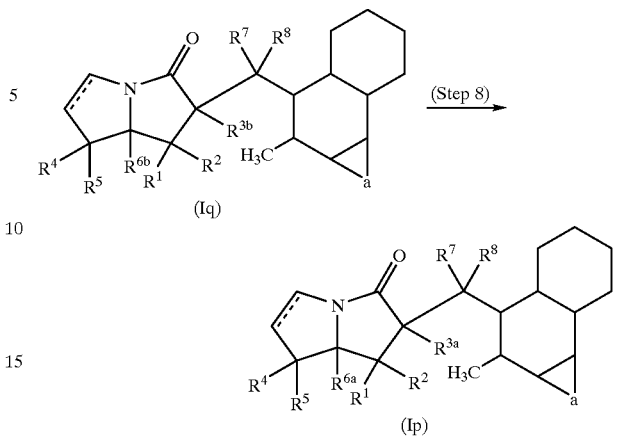

{wherein $R^1$, $R^2$, $R^4$, $R^5$, $R^7$, $R^8$, a and ---- have the same meanings as defined above, respectively; at least one of $R^{3a}$ and $R^{6a}$ represents $OR^{15a}$ (wherein $R^{15a}$ has the same meaning as defined above; and wherein, when $R^{3a}$ is not $OR^{15a}$ (wherein $R^{15a}$ has the same meaning as defined above), $R^{3a}$ represents a group excluding $OR^{15a}$ (wherein $R^{15a}$ has the same meaning as defined above) from the definition of $R^3$, and when $R^{6a}$ is not $OR^{15a}$ (wherein $R^{15a}$ has the same meaning as defined above), $R^{6a}$ represents a group excluding $OR^{15a}$ (wherein $R^{15a}$ has the same meaning as defined above) from the definition of $R^6$); and at least one of $R^{3b}$ and $R^{6b}$ represents hydroxy (wherein, when $R^{3b}$ is not hydroxy, $R^{3b}$ represents a group excluding hydroxy from the definition of $R^3$, and when $R^{6b}$ is not hydroxy, $R^{6b}$ represents a group excluding hydroxy from the definition of $R^6$)}.

Step 8:

Compound (Ip) can be produced by reacting Compound (Iq) which is Compound (I) wherein $R^3$ and/or $R^6$ represents hydroxy with a halide represented by $R^{15a}X$ (wherein $R^{15a}$ and X have the same meanings as defined above) in an inert solvent in the presence of a base.

The inert solvent includes ethers such as tetrahydrofuran, dioxane, etc.; dimethylformamide; dichloromethane; and the like. The base includes sodium hydride, potassium tert-butoxide, isopropylethylamine, lithium diisopropylamide and the like, which are used in an amount of 1 to 5 equivalents based on Compound (Iq) as the starting material.

The halide represented by $R^{15a}X$ (wherein $R^{15a}$ and X have the same meanings as defined above) is used in an amount of 1 to 10 equivalents based on Compound (Iq) as the starting material, and if necessary, sodium iodide or potassium iodide may be added in an amount of 1 to 10 equivalents. The reaction is completed at −78° C. to the boiling point of the used solvent, preferably at 0 to 30° C., in 1 to 48 hours.

Production Method 9

Compound (Ir) which is Compound (I) wherein $R^3$ and/or $R^6$ represents $OR^{15b}$ (wherein $R^{15b}$ represents substituted or unsubstituted lower alkanoyl) can be produced by the following reaction step.

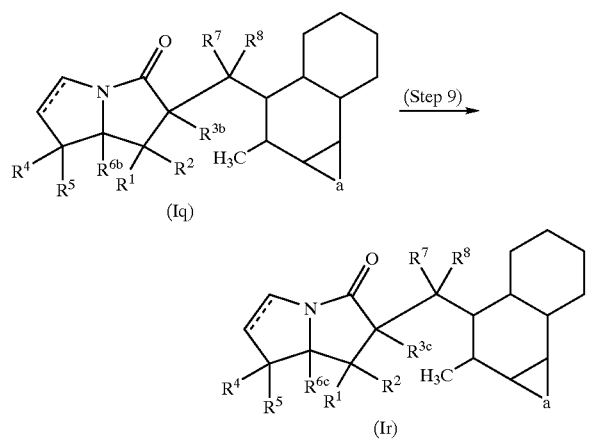

(Iq)

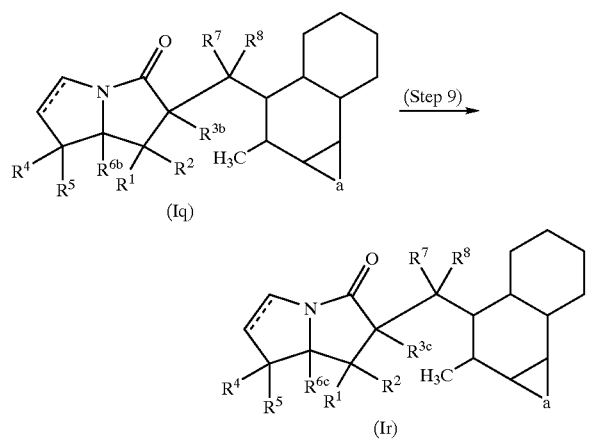

(Ir)

{wherein $R^1$, $R^2$, $R^{3b}$, $R^4$, $R^5$, $R^{6b}$, $R^7$, $R^8$, a and ---- have the same meanings as defined above, respectively; at least one of $R^{3a}$ and $R^{6c}$ represents $OR^{15b}$ (wherein $R^{15b}$ has the same meaning as defined above; and wherein, when $R^{3c}$ is not $OR^{15b}$ (wherein $R^{15b}$ has the same meaning as defined above), $R^{3c}$ represents a group excluding $OR^{15b}$ (wherein $R^{15b}$ has the same meaning as defined above) from the definition of $R^3$, and when $R^{6c}$ is not $OR^{15b}$ (wherein $R^{15b}$ has the same meaning as defined above), $R^{6c}$ represents a group excluding $OR^{15b}$ (wherein $R^{15b}$ has the same meaning as defined above) from the definition of $R^6$)}.

Step 9:

Compound (Ir) can be obtained by reacting Compound (Iq) which is Compound (I) wherein $R^3$ and/or $R^6$ is hydroxy with 1 to 10 equivalents of a reactive derivative of a carboxylic acid represented by $R^{15b}OH$ (wherein $R^{15b}$ has the same meaning as defined above) in an inert solvent, if necessary, in the presence of a base.

The inert solvent includes dichloromethane, chloroform, dimethylformamide and the like. The reactive derivative of a carboxylic acid includes an acid halide, an acid anhydride, a mixed acid anhydride and the like. The base is preferably a tertiary amine such as pyridine, 4-dimethylaminopyridine, triethylamine, diisopropylethylamine or the like, which may be used as the solvent at the same time. The reaction is completed at 0° C. to the boiling point of the used solvent, preferably at 20 to 30° C., in 1 to 48 hours.

Production Method 10

Compound (Is) which is Compound (I) wherein $R^1$ represents hydrogen, $R^2$ and $R^3$ are combined to represent —O— and $R^4$ represents $CONR^{16}$ (wherein $R^{16}$ has the same meaning as defined above) or $CONR^{17}R^{18}$ (wherein $R^{17}$ and $R^{18}$ have the same meanings as defined above, respectively) can be produced by the following reaction step.

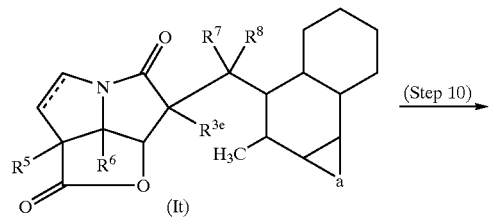

(It)

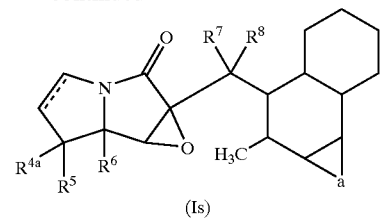

(Is)

{wherein $R^5$, $R^6$, $R^7$, $R^8$, a and ---- have the same meanings as defined above, respectively; $R^{3a}$ represents bromine or iodine; and $R^{4a}$ represents $COOR^{16}$ (wherein $R^{16}$ has the same meaning as defined above) or $CONR^{17}R^{18}$ (wherein $R^{17}$ and $R^{18}$ have the same meanings as defined above, respectively)}.

Step 10:

Compound (Is) can be obtained by reacting Compound (It) which is Compound (I) wherein $R^1$ is hydrogen, $R^3$ is bromine or iodine and $R^2$ and $R^4$ are combined to represent —O(C=O)— with 1 equivalent to a solvent amount, preferably 10 equivalents or more, of water or an alcohol represented by $HOR^{16}$ (wherein $R^{16}$ has the same meaning as defined above) or an amine represented by $HNR^{17}R^{18}$ (wherein $R^{17}$ and $R^{18}$ have the same meanings as defined above, respectively) in an inert solvent, if necessary, in the presence of a base.

The inert solvent includes dichloromethane, dimethylformamide, tetrahydrofuran and the like. The alcohol includes lower alcohols such as methanol, ethanol, allyl alcohol and the like, which may be used as the solvent at the same time. The base includes potassium carbonate, sodium carbonate, sodium bicarbonate, sodium hydroxide, potassium hydroxide, triethylamine, diisopropylethylamine, dimethylaminopyridine and the like, which are used in an amount of 1 to 10 equivalents. Any primary amine or secondary amine is used as the amine. Examples thereof include dialkylamines such as dimethylamine, diethylamine and the like; and cyclic amines such as morpholine, piperidine, piperazine and the like. The reaction is completed at −20° C. to the boiling point of the used solvent, preferably at 0 to 30° C., in 1 to 48 hours.

Production Method 11

Compound (Ikb) which is Compound (I) wherein $R^1$ represents $OR^{13a}$ (wherein $R^{13a}$ represents substituted or unsubstituted lower alkyl, substituted or unsubstituted lower alkenyl, or substituted or unsubstituted lower alkynyl) can be produced by the following reaction step.

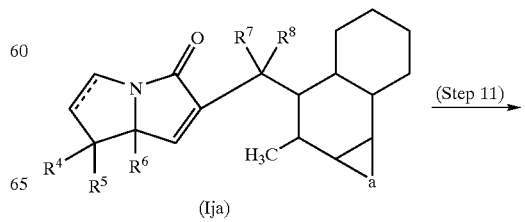

(Ija)

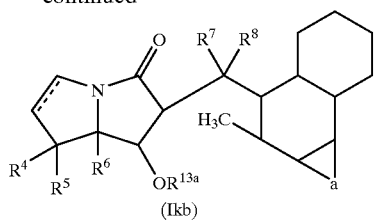

(Ikb)

(wherein $R^4$, $R^5$, $R^6$, $R^7$, $R^8$, $R^{13a}$, a and ---- have the same meanings as defined above, respectively).

Step 11:

Compound (Ikb) can be obtained by reacting Compound (Ija) which is Compound (I) wherein $R^1$ is hydrogen and $R^2$ and $R^3$ are combined to represent a bond with 1 equivalent to a solvent amount of a lower alcohol represented by $HOR^{13a}$ (wherein $R^{13a}$ has the same meaning as defined above) in an inert solvent in the presence of an acid catalyst.

The inert solvent includes dichloromethane, chloroform, dimethylformamide, tetrahydrofuran, dioxane, toluene and the like. The acid catalyst includes trifluoroacetic acid, p-toluenesulfonic acid and the like, which are used in an amount of 0.01 to 10 equivalents. The reaction is completed at 0° C. to the boiling point of the used solvent, preferably at 0 to 30° C., in 1 to 72 hours.

When Compound (Ija) wherein $R^6$ is $OR^{19}$ (wherein $R^{19}$ has the same meaning as defined above) is used as the starting material, a compound which is Compound (Ikb) wherein $R^6$ is $OR^{13a}$ (wherein $R^{13a}$ has the same meaning as defined above) may be obtained.

Production Method 12

Compound (Iu) which is Compound (I) wherein $R^2$ and $R^3$ are combined to represent —CH=N—NH— or Compound (Iv) which is Compound (I) wherein $R^1$ is methyl and $R^2$ and $R^3$ are combined to represent a bond can be produced by the following reaction step.

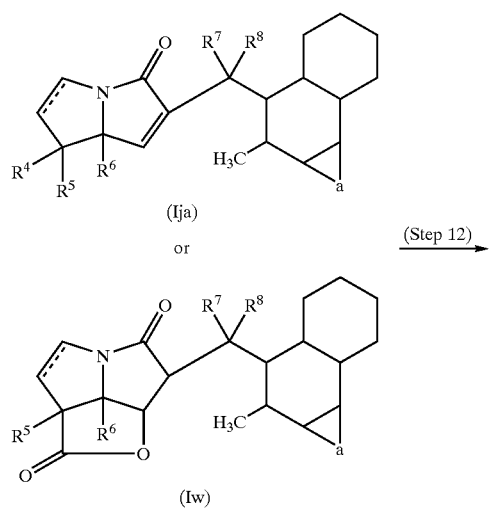

(Ija)

or (Step 12) →

(Iw)

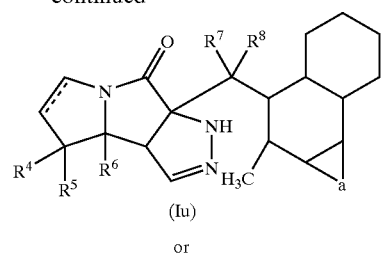

(Iu)

or

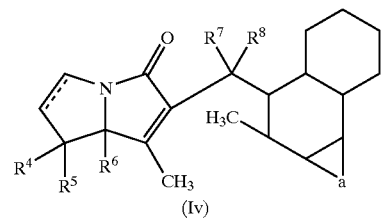

(Iv)

(wherein $R^4$, $R^5$, $R^6$, $R^7$, $R^8$, a and ---- have the same meanings as defined above, respectively).

Step 12:

Compound (Iu) or Compound (Iv) can be obtained by treating Compound (Ija) which is Compound (I) wherein $R^1$ is hydrogen and $R^2$ and $R^3$ are combined to represent a bond, or Compound (Iw) which is Compound (I) wherein $R^2$ and $R^4$ are combined to represent —O(C=O)—, $R^1$ represents hydrogen and $R^3$ represents hydrogen with 1 equivalent to an excess amount of diazomethane in an inert solvent.

The inert solvent includes ethers such as ether, tetrahydrofuran, dioxane and the like; and alcohols such as methanol, ethanol and the like, which are used alone or as a mixture. The reaction is completed at −20° C. to the boiling point of the used solvent, preferably at 0 to 20° C., in 0.1 to 1 hour.

Compound (I) having a desired functional group at a desired position can be obtained by carrying out the reaction using an optional combination of the above methods and methods generally used in the synthetic organic chemistry.

The desired compound in each of the above production methods can be isolated and purified by subjecting it to the purification method generally used in the synthetic organic chemistry, e.g., filtration, extraction, washing, drying, concentration, recrystallization, various types of chromatography or the like.

When it is desirable to obtain a salt of Compound (I), Compound (I) may be purified as such when it is obtained in the form of a salt, and when it is obtained in the free form, it may be isolated and purified by a usual method, namely by dissolving or suspending Compound (I) in an appropriate solvent and then adding a desired acid, metal or base thereto to effect formation of the salt.

In addition, Compound (I) and a pharmaceutically acceptable salt thereof may exist in the form of an addition product with water or various solvents, and these addition products are also included in the present invention.

Compound (I) or a pharmaceutically acceptable salt thereof can be used as such or in various preparation forms according to its pharmacological actions and purposes of administration. Pharmaceutical compositions of the present invention can be produced by uniformly mixing Compound (I) or a pharmaceutically acceptable salt thereof, in an amount effective as the active ingredient, with a pharmaceutically acceptable carrier. The carrier can take a wide variety of forms according to each preparation form desirable for the administration. It is desirable that the pharmaceutical composition is in a unit dosage form suitable for its oral or parenteral administration such as injection or the like.

In preparing tablets, for example, fillers such as lactose, glucose, sucrose, mannitol, methyl cellulose or the like; disintegrators such as starch, sodium alginate, carboxymethyl cellulose calcium, crystalline cellulose or the like; lubricants such as magnesium stearate, talc or the like; binders such as gelatin, polyvinyl alcohol, polyvinyl pyrrolidone, hydroxypropyl cellulose, methyl cellulose or the like; surfactants such as a sucrose fatty acid ester, a sorbitol fatty acid ester or the like; or the like may be used in accordance with the usual method. Tablets containing 1 to 300 mg of the active ingredient per one tablet are preferable.

In preparing granules, for example, fillers such as lactose, sucrose or the like, disintegrators such as starch or the like, binders such as gelatin or the like, or the like may be used in the usual way. In preparing powders, for example, fillers such as lactose, mannitol or the like, or the like may be used in accordance with the usual method. In preparing capsules, for example, gelatin, water, sucrose, acacia, sorbitol, glycerol, crystalline cellulose, magnesium stearate, talc or the like may be used in the usual way. Capsules containing 1 to 300 mg of the active ingredient per one capsule are preferable.

In preparing injections, solvents such as water, physiological saline, plant oil (e.g., olive oil, peanut oil or the like), ethyl oleate, propylene glycol or the like; solubilizing agents such as sodium benzoate, sodium salicylate, urethane or the like; isotonicity agents such as sodium chloride, glucose or the like; preservatives such as phenol, cresol, a p-hydroxybenzoic acid ester, chlorobutanol or the like; antioxidants such as ascorbic acid, sodium pyrosulfite or the like; or the like may be used in the usual way.

Compound (I) or a pharmaceutically acceptable salt thereof can be administered by an oral method or a parenteral method using injections or the like. Although its effective dose and administration frequency vary depending on the administration form, the age or body weight of the patient, symptoms of the disease and the like, it is generally preferable to administer it 1 to 4 times per day at a dose of 0.01 to 20 mg/kg per day.

Examples of Compound (I) obtained by the present invention are shown in the following Table 1 (1) to Table 1 (9), although the scope of the present invention is not limited to these compounds.

TABLE 1

| Compound No. | Structure |
|---|---|
| 1 | |
| 2 | 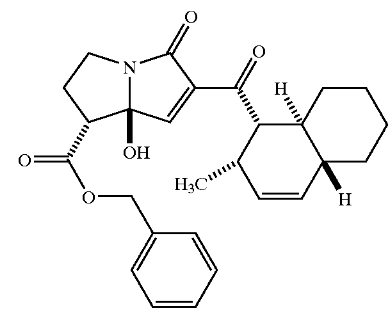 |
| 3 | 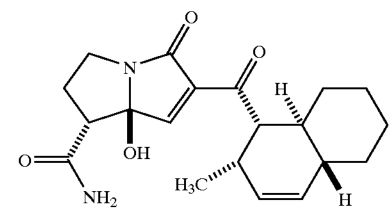 |
| 4 | 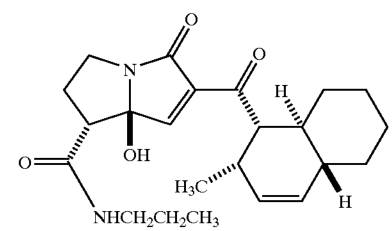 |
| 5 | 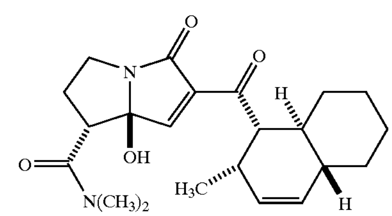 |
| 6 | 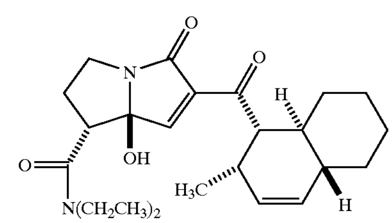 |
| 7 | 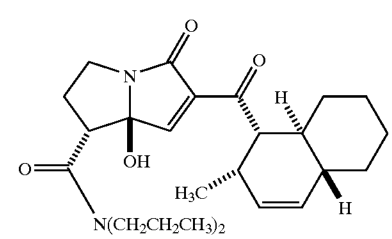 |

TABLE 1-continued

| Compound No. | Structure |
|---|---|
| 8 | |
| 9 | |
| 10 | |
| 11 | |
| 12 | |
| 13 | 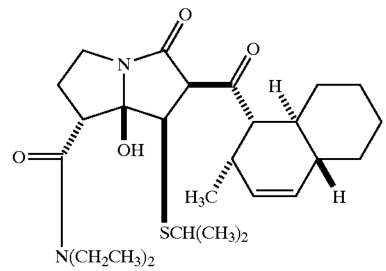 |
| 14 | 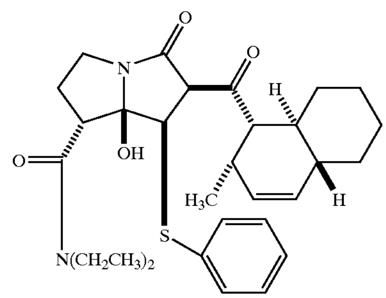 |
| 15 | 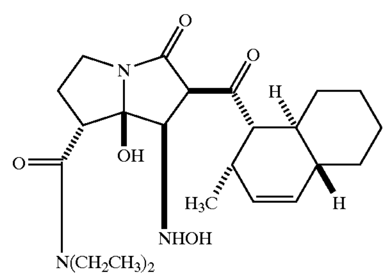 |
| 16 | 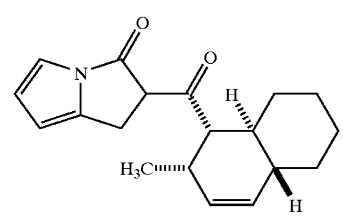 |
| 17 | 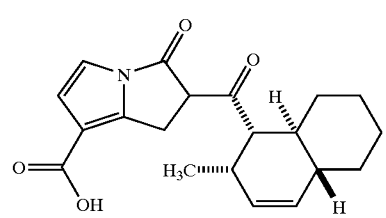 |
| 18 | 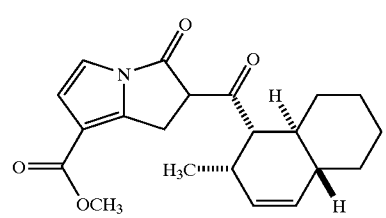 |

TABLE 1-continued

| Compound No. | Structure |
|---|---|
| 19 | 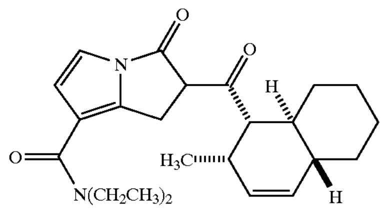 |
| 20 | 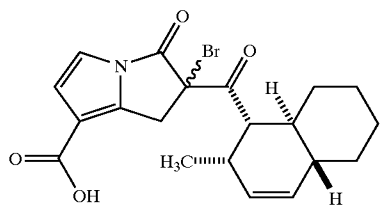 |
| 21 | 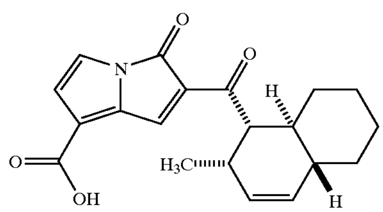 |
| 22 | 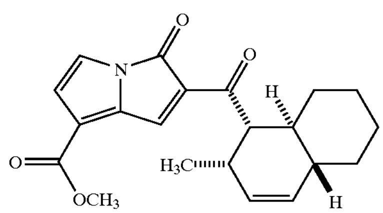 |
| 23 | 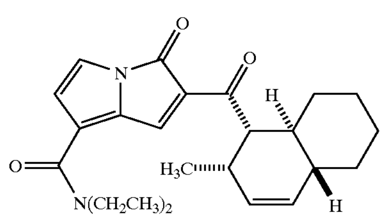 |
| 24 | 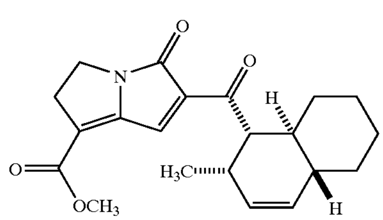 |
| 25 | 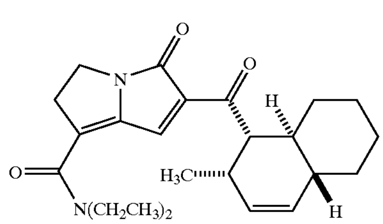 |
| 26 | |
| 27 | |
| 28 | |
| 29 | |
| 30 | |
| 31 | |

TABLE 1-continued

| Compound No. | Structure |
|---|---|
| 32 | 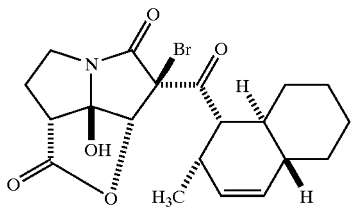 |
| 33 | 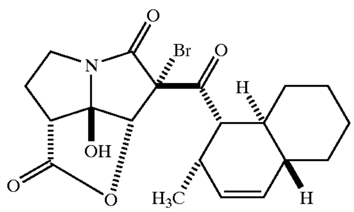 |
| 34 | 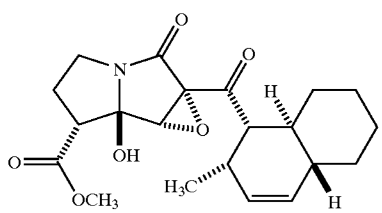 |
| 35 | 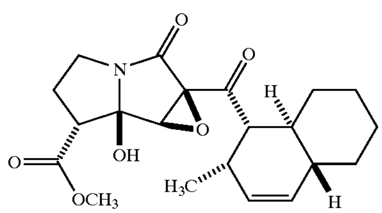 |
| 36 | 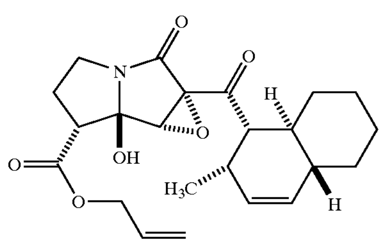 |
| 37 | 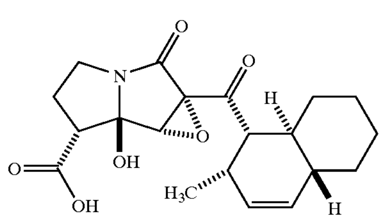 |
| 38 | 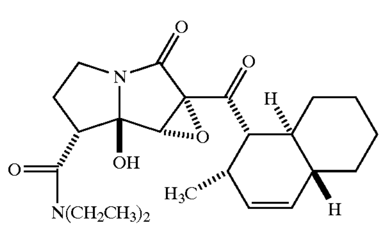 |
| 39 | |
| 40 | |
| 41 | |
| 42 | |
| 43 | |
| 44 | |

TABLE 1-continued

| Compound No. | Structure |
|---|---|
| 45 | (structure image) |

Next, biological activities of specific Compounds (I) are described based on test examples.

TEST EXAMPLE 1
Antibacterial Activity:

Antibacterial activities (minimum inhibitory concentration (MIC: mg/ml)) of Compounds (I) on various bacteria are shown in Table 2. The antibacterial activity was measured by an agar dilution method using a medium comprising 3 g/L Bacto-Tryptone (manufactured by Difco), 3 g/L meat extract, 1 g/L yeast extract, 1 g/L glucose and 16 g/L agar.

TABLE 2

| Compound No. | ER[1] | SA[2] | BS[3] |
|---|---|---|---|
| 1 | 0.52 | 1.0 | 0.52 |
| 6 | 3.6 | 3.6 | 1.8 |
| 7 | 5.0 | 10 | 1.3 |
| 8 | 1.5 | 12 | 0.38 |
| 32 | 13 | 53 | 13 |
| 36 | 48 | 95 | 48 |
| 38 | 8.1 | 33 | 16 |

[1]*Enterocccus hirae* ATCC 10541
[2]*Staphylococcus aureus* ATCC 6538P
[3]*Bacillus subtilis* ATCC 10707

TEST EXAMPLE 2
Growth Inhibition Action on Human Renal Carcinoma Cell Line ACHN:

Cells of human renal carcinoma cell line ACHN adjusted to a density of $3 \times 10^4$ cells/ml with RPMI (Roswell Park Memorial Institute) medium comprising 10% fetal bovine serum and 2 mmol/l glutamine were dispensed in a volume of 50 μl into each well of a 96 well microtiter plate and cultured at 37° C. for 24 hours in a carbon dioxide incubator. Each of the test compounds serially diluted with the above medium was added to each well in a volume of 50 μl, following by culturing at 37° C. for 72 hours in a carbon dioxide incubator. After discarding the culture supernatant, each well was washed twice with 0.1 ml of phosphate buffered saline (PBS), and then 0.1 ml of the above medium was again added to each well. Cell proliferation kit II (Boehringer Mannheim) was used for the measurement of the number of cells in each well. After addition of a color-producing reagent and subsequent incubation at 37° C. for 3 hours in a carbon dioxide incubator, absorbance at 490 nm and 655 nm was measured using a microplate reader, and a value (differential absorbance) was calculated by subtracting the absorbance at 655 nm from the absorbance at 490 nm in each well. By comparing the differential absorbance obtained from untreated cells and that obtained from cells treated with a predetermined concentration of each test compound, the concentration of the test compound capable of inhibiting 50% of the cell growth was calculated and expressed as $IC_{50}$. The results are shown in Table 3.

TABLE 3

| Compound No. | $IC_{50}$ (μM) |
|---|---|
| 1 | 4.4 |
| 6 | 5.6 |
| 8 | 2.7 |
| 12 | 5.7 |
| 16 | 64 |

According to Table 2 and Table 3, Compound (I) has excellent antitumor activity and is useful as a therapeutic agent for malignant tumors. It is also useful as an antibacterial agent.

BEST MODE FOR CARRYING OUT THE INVENTION

Examples are shown in the following. Physicochemical data of each compound in the following examples were measured using the following instruments.

$^1$H NMR: Bruker DMX 500 (500 MHz) JEOL Alpha 400 (400 MHz) JEOL Lambda 300 (300 MHz).

FABMS JEOL JMS-HX110.

In the following examples, UCS 1025A represented by the following formula (Xa) and UCS 1025B represented by the following formula (Xb) were used as the starting materials.

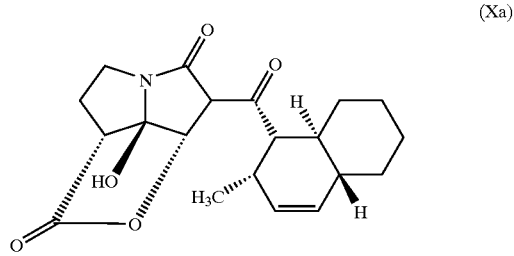

(Xa)

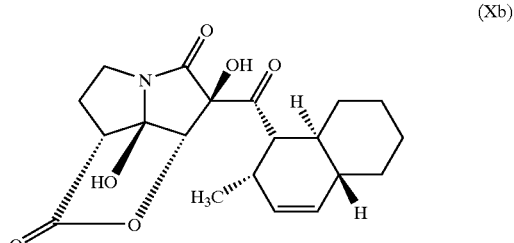

(Xb)

EXAMPLE 1

Compound 1

UCS 1025A (100 mg, 0.280 mmol) was dissolved in dimethylformamide (6 ml), and sodium carbonate (30 mg, 0.28 mmol) and iodomethane (0.52 ml, 8.4 mmol) were added thereto, followed by stirring at room temperature for 18 hours. Water was added to the reacting mixture, and the mixture was extracted with ethyl acetate. The organic layer was washed with water and saturated brine and then dried over anhydrous sodium sulfate. The solvent was evaporated under a reduced pressure, and the resulting residue was purified by silica gel column chromatography (2:1= hexane:ethyl acetate) to obtain Compound 1 (39 mg, 37%).

¹H NMR (500 MHz, CDCl$_3$) δ 0.79 (d, J=7.1 Hz, 3H), 0.85 (m, 1H), 1.10 (m, 1H), 1.2–1.9 (m, 8H), 2.5–2.6 (m, 2H), 2.71 (ddt, J=6.8, 13.2, 9.0 Hz, 1H), 3.18 (d, J=6.8 Hz, 1H), 3.35 (ddd, J=11.0, 9.0, 2.9 Hz, 1H), 3.52 (dd, J=11.3, 5.7 Hz, 1H), 3.59 (s, 3H), 3.79 (dt, J=11.0, 9.0 Hz, 1H), 5.39 (d, J=9.8 Hz, 1H), 5.53 (ddd, J=9.8, 4.6, 2.5 Hz, 1H), 7.48 (s, 1H).

FABMS m/z 374 (M+H)$^+$ C$_{21}$H$_{27}$NO$_5$=373.

EXAMPLE 2

Compound 2

UCS 1025A (20 mg, 0.056 mmol) was dissolved in dimethylformamide (2 ml), and sodium carbonate (6.0 mg, 0.056 mmol) and benzyl bromide (0.020 ml, 0.17 mmol) were added thereto, followed by stirring at room temperature for 1 hour. Water was added to the reaction mixture, and the mixture was extracted with ethyl acetate. The organic layer was washed with water and saturated brine and then dried over anhydrous sodium sulfate. The solvent was evaporated over a reduced pressure, and the resulting residue was purified by silica gel column chromatography (1:1=hexane:ethyl acetate) to obtain Compound 2 (17 mg, 68%).

¹H NMR (300 MHz, CDCl$_3$) δ 0.78 (d, J=7.2 Hz, 3H), 1.0–1.9 (m, 10H), 2.5–2.8 (m, 4H), 3.28 (dd, J=7.1, 2.1 Hz, 1H), 3.35 (m, 1H), 3.54 (dd, J=11.2, 5.7 Hz, 1H), 3.80 (dt, J=11.2, 8.6 Hz, 1H), 4.95 (d, J=12.1 Hz, 1H), 5.00 (d, J=12.3 Hz, 1H), 5.39 (br d, J=9.9 Hz, 1H), 5.53 (ddd, J=9.7, 4.4, 2.6 Hz, 1H), 7.3–7.4 (m, 5H), 7.49 (s, 1H).

FABMS m/z 450 (M+H)$^+$ C$_{27}$H$_{31}$NO$_5$=449.

EXAMPLE 3

Compounds 3 and 45

UCS 1025A (200 mg, 0.557 mmol) was dissolved in dimethylformamide (10 ml), and 2-chloro-1-methylpyridinium iodide (711 mg, 2.79 mmol) was added thereto, followed by stirring at room temperature for 35 minutes. A methanol solution of ammonia (about 6.8 mol/L, 0.82 ml, 5.6 mmol) was added thereto, followed by stirring at room temperature for 25 minutes. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was recrystallized from ethyl acetate to obtain Compound 3 (85 mg, 43%). The mother liquor was concentrated and the residue was purified by preparative thin layer chromatography (9:1=chloroform:methanol) to obtain Compound 3 (12 mg, 6%) and Compound 45 (39 mg, 20%).

Compound 3:

¹H NMR (300 MHz, CDCl$_3$) δ 0.66 (d, J=7.2 Hz, 3H), 0.7–1.5 (m, 5H), 1.6–1.9 (m, 5H), 2.23 (m, 1H), 2.4–2.5 (m, 2H), 2.93 (d, J=5.9 Hz, 1H), 3.12 (m, 1H), 3.4–3.6 (m, 2H), 5.37 (d, J=9.9 Hz, 1H), 5.54 (ddd, J=9.7, 4.2, 2.4 Hz, 1H), 6.54 (s, 1H), 6.96 (br s, 1H), 7.52 (br s, 1H), 7.59 (s, 1H).

FABMS m/z 359 (M+H)$^+$ C$_{20}$H$_{26}$N$_2$O$_4$=358.

Compound 45:

¹H NMR (300 MHz, CDCl$_3$) δ 0.78 (d, J=7.0 Hz, 3H), 0.8–1.8 (m, 10H), 2.4–2.7 (m, 2H), 2.92 (m, 1H), 3.05 (dd, J=9.2, 2.4 Hz, 1H), 3.13 (dd, J=11.2, 5.5 Hz, 1H), 3.33 (ddd, J=11.9., 9.7, 5.5 Hz, 1H), 3.81 (m, 1H), 3.82 (s, 1H), 4.04 (s, 1H), 4.82 (s, 1H), 5.40 (d, J=9.9 Hz, 1H), 5.59 (ddd, J=9.9, 4.8, 2.4 Hz, 1H), 6.61 (br s, 1H).

FABMS m/z 359 (M+H)$^+$ C$_{20}$H$_{26}$N$_2$O$_4$=358.

EXAMPLE 4

Compound 4

UCS 1025A (20 mg, 0.056 mmol) was dissolved in dichloromethane (5 ml), and 2-chloro-1-methylpyridinium iodide (42 mg, 0.17 mmol) and propylamine (0.014 ml, 0.17 mmol) were added thereto, followed by stirring at room temperature for 45 minutes. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was purified by silica gel column chromatography (ethyl acetate) to obtain Compound 4 (10 mg, 45%).

¹H NMR (300 MHz, CDCl$_3$) δ 0.78 (d, J=7.2 Hz, 3H), 0.88 (t, J=7.4 Hz, 3H), 1.0–1.9 (m, 12H), 2.3–2.7 (m, 3H), 2.94 (dd, J=7.0, 2.6 Hz, 1H), 3.0–3.3 (m, 3H), 3.32 (m, 1H), 3.56 (dd, J=11.0, 5.1 Hz, 1H), 3.89 (dt, J=11.2, 8.1 Hz, 1H), 5.38 (br d, J=9.7 Hz, 1H), 5.53 (ddd, J=9.9, 4.4, 2.5 Hz, 1H), 5.86 (br s, 1H), 7.46 (s, 1H).

FABMS m/z 401 (M+H)$^+$ C$_{23}$H$_{32}$N$_2$O$_4$=400.

EXAMPLE 5

Compound 5

UCS 1025A (20 mg, 0.056 mmol) was dissolved in dichloromethane (5 ml), and 2-chloro-1-methylpyridinium iodide (71 mg, 0.28 mmol) and dimethylamine (a 2 mol/L tetrahydrofuran solution, 0.14 ml, 0.28 mmol) were added thereto, followed by stirring at room temperature for 1 hour. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was purified by preparative thin layer chromatography (ethyl acetate) to obtain Compound 5 (5.2 mg, 24%).

¹H NMR (300 MHz, CDCl$_3$) δ 0.78 (d, J=7.2 Hz, 3H), 1.0–2.0 (m, 10H), 2.4–2.7 (m, 3H), 2.85 (S, 3H), 3.16 (S, 3H), 3.30 (m, 1H), 3.44 (dd, J=11.2, 5.7 Hz, 1H), 3.5–3.6 (m, 2H), 3.89 (m, 1H), 5.38 (d, J=9.7 Hz, 1H), 5.51 (m, 1H), 7.30 (S, 1H).

FABMS m/z 387 (M+H)$^+$ C$_{22}$H$_{30}$N$_2$O$_4$=386.

EXAMPLE 6

Compound 6

UCS 1025A (120 mg, 0.334 mmol) was dissolved in dichloromethane (20 ml), and 2-chloro-1-methylpyridinium iodide (426 mg, 1.67 mmol) was added thereto, followed by stirring at room temperature for 20 minutes. Then, diethylamine (0.173 ml, 1.67 mmol) was added thereto, followed by stirring at room temperature for 20 minutes. Water was added thereto and the mixture was extracted with chloroform. The organic layer was washed with saturated brine and then dried over anhydrous sodium sulfate. The solvent was evaporated under a reduced pressure, and the resulting residue was purified by silica gel column chromatography (2:3=hexane:ethyl acetate) to obtain Compound 6 (100 mg, 70%).

¹H NMR (400 MHz, CDCl$_3$) δ 0.77 (d, J=7.3 Hz, 3H), 0.80 (m, 1H), 0.99 (t, J=7.1 Hz, 3H), 1.16 (m, 1H), 1.22 (t, J=7.1 Hz, 3H), 1.31 (m, 2H), 1.50 (m, 1H), 1.6–1.9 (m, 5H), 2.4–2.7 (m, 3H), 2.62 (s, 1H), 2.98 (m, 1H), 3.2–3.4 (m, 2H), 3.40 (dd, J=7.1, 2.7 Hz, 1H), 3.57 (m, 2H), 3.65 (dd, J=11.2, 5.6 Hz, 1H), 3.94 (dt, J=10.5, 8.1 Hz, 1H), 5.38 (br d, J=9.5 Hz, 1H), 5.52 (ddd, J=9.8, 4.6, 2.7 Hz, 1H), 7.36 (s, 1H).

FABMS m/z 415 (M+H)+ $C_{24}H_{34}N_2O_4$=414.

EXAMPLE 7

Compound 7

UCS 1025A (20 mg, 0.056 mmol) was dissolved in dichloromethane (4 ml), and 2-chloro-1-methylpyridinium iodide (71 mg, 0.28 mmol) and dipropylamine (0.038 ml, 0.28 mmol) were added thereto, followed by stirring at room temperature for 35 minutes. Water was added to the reaction mixture, and the mixture was extracted with ethyl acetate. The organic layer was washed with saturated brine and then dried over anhydrous sodium sulfate. The solvent was evaporated under a reduced pressure, and the resulting residue was purified by preparative thin layer chromatography (7:1=chloroform:acetonitrile) to obtain Compound 7 (16 mg, 65%).

$^1$H NMR (400 MHz, CDCl$_3$) δ 0.77 (d, J=7.2 Hz, 3H), 0.81 (t, J=7.3 Hz, 3H), 0.96 (t, J=7.3 Hz, 3H), 1.0–1.9 (m, 14H), 2.4–3.0 (m, 4H), 3.1–3.7 (m, 6H), 3.93 (m, 1H), 5.37 (d, J=9.5 Hz, 1H), 5.53 (ddd, J=9.5, 4.4, 2.4 Hz, 1H), 7.36 (s, 1H).

FABMS m/z 443 (M+H)+ $C_{26}H_{38}N_2O_4$=442.

EXAMPLE 8

Compound 8

UCS 1025A (20 mg, 0.056 mmol) was dissolved in dichloromethane (4 ml), and 2-chloro-1-methylpyridinium iodide (71 mg, 0.28 mmol) and dibutylamine (0.047 ml, 0.28 mmol) were added thereto, followed by stirring at room temperature for 15 minutes. Water was added to the reaction mixture, and the mixture was extracted with ethyl acetate. The organic layer was washed with saturated brine and then dried over anhydrous sodium sulfate. The solvent was evaporated under a reduced pressure, and the resulting residue was purified by preparative thin layer chromatography (7:1=chloroform:acetonitrile) to obtain Compound 8 (16 mg, 61%).

$^1$H NMR (400 MHz, CDCl$_3$) δ 0.76 (d, J=7.2 Hz, 3H), 0.88 (t, J=7.3 Hz, 3H), 0.98 (t, J=7.3 Hz, 3H), 1.0–2.0 (m, 18H), 2.4–2.7 (m, 3H), 2.87 (m, 1H), 3.1–3.6 (m, 6H), 3.89 (m, 1H), 5.37 (d, J=9.9 Hz, 1H), 5.52 (m, 1H), 7.29 (s, 1H).

FABMS m/z 471 (M+H)+ $C_{28}H_{42}N_2O_4$=470.

EXAMPLE 9

Compound 9

UCS 1025A (20 mg, 0.056 mmol) was dissolved in dichloromethane (4 ml), and 2-chloro-1-methylpyridinium iodide (71 mg, 0.28 mmol) and N-methylbutylamine (0.029 ml, 0.28 mmol) were added thereto, followed by stirring at room temperature for 4 hours. Water was added to the reaction mixture, and the mixture was extracted with ethyl acetate. The organic layer was washed with saturated brine and then dried over anhydrous sodium sulfate. The solvent was evaporated under a reduced pressure, and the resulting residue was purified by preparative thin layer chromatography (7:1=chloroform:acetonitrile) to obtain Compound 9 (7.6 mg, 33%).

$^1$H NMR (main rotational isomer) (400 MHz, CDCl$_3$) δ 0.77 (d, J=7.0 Hz, 3H), 0.82 (t, J=7.3 Hz, 3H), 1.0–1.9 (m, 12H), 2.4–2.7 (m, 3H), 3.0–4.0 (m, 6H), 3.13 (s, 3H), 5.37 (d, J=9.7 Hz, 1H), 5.52 (ddd, J=9.7, 4.6, 2.4 Hz, 1H), 7.34 (s, 1H).

FABMS m/z 415 (M+H)+ $C_{24}H_{34}N_2O_4$=414.

EXAMPLE 10

Compound 10

UCS 1025A (20 mg, 0.056 mmol) was dissolved in dichloromethane (4 ml), and 2-chloro-1-methylpyridinium iodide (71 mg, 0.28 mmol) and N-methylbenzylamine (0.036 ml, 0.28 mmol) were added thereto, followed by stirring at room temperature for 19 hours. Water was added to the reaction mixture, and the mixture was extracted with ethyl acetate. The organic layer was washed with saturated brine and then dried over anhydrous sodium sulfate. The solvent was evaporated under a reduced pressure, and the resulting residue was purified by preparative thin layer chromatography (7:1=chloroform:acetonitrile) to obtain Compound 10 (7.0 mg, 27%).

$^1$H NMR (main rotational isomer) (400 MHz, CDCl$_3$) δ 0.78 (d, J=7.0 Hz, 3H), 1.0–2.0 (m, 10H), 2.4–2.7 (m, 3H), 3.05 (s, 3H), 3.2–4.0 (m, 4H), 4.42 (d, J=14.3 Hz, 1H), 4.57 (d, J=14.3 Hz, 1H), 5.39 (d, J=9.5 Hz, 1H), 5.60 (m, 1H), 7.1–7.5 (m, 5H), 7.29 (s, 1H).

FABMS m/z 463 (M+H)+ $C_{28}H_{34}N_2O_4$=462.

EXAMPLE 11

Compound 11

UCS 1025A (20 mg, 0.056 mmol) was dissolved in dichloromethane (4 ml), and 2-chloro-1-methylpyridinium iodide (71 mg, 0.28 mmol) and piperidine (0.028 ml, 0.28 mmol) were added thereto, followed by stirring at room temperature for 18 hours. Water was added to the reaction mixture, and the mixture was extracted with ethyl acetate. The organic layer was washed with saturated brine and then dried over anhydrous sodium sulfate. The solvent was evaporated under a reduced pressure, and the resulting residue was purified by preparative thin layer chromatography (1:2=hexane:ethyl acetate) to obtain Compound 11 (5.7 mg, 24%).

$^1$H NMR (300 MHz, CDCl$_3$) δ 0.77 (d, J=7.2 Hz, 3H), 1.0–2.0 (m, 16H), 2.4–2.7 (m, 3H), 3.2–3.7 (m, 8H), 3.87 (m, 1H), 5.37 (d, J=9.9 Hz, 1H), 5.52 (ddd, J=9.7, 4.6, 2.6 Hz, 1H), 7.31 (s, 1H).

FABMS m/z 427 (M+H)+ $C_{25}H_{34}N_2O_4$=426.

EXAMPLE 12

Compound 12

Compound 6 (17 mg, 0.041 mmol) was dissolved in dimethyl sulfoxide (3 ml), and a potassium phosphate buffer (10 mmol/L, pH=7.0, 12 ml) and ethanethiol (0.0060 ml, 0.082 mmol) were added thereto, followed by stirring at room temperature for 1 hour. Water was added to the reaction mixture, and the mixture was extracted with ethyl acetate. The organic layer was washed with saturated brine and then dried over anhydrous sodium sulfate. The solvent was evaporated under a reduced pressure, and the resulting residue was triturated with hexane to obtain Compound 12 (12 mg, 61%).

$^1$H NMR (300 MHz, CDCl$_3$) δ 0.82 (d, J=7.1 Hz, 3H), 0.9–2.0 (m, 10H), 1.18 (t, J=7.1 Hz, 3H), 1.22 (t, J=7.2 Hz, 3H), 1.26 (t, J=7.4 Hz, 3H), 2.18 (m, 1H), 2.5–2.7 (m, 3H), 3.17 (dd, J=7.5, 2.0 Hz, 1H), 3.2–3.3 (m, 3H), 3.5–3.6 (m, 3H), 3.59 (dd, J=11.3, 5.8 Hz, 1H), 3.7–3.8 (m, 1H), 3.77 (d, J=9.7 Hz, 1H), 4.09 (s, 1H), 4.41 (d, J=9.7 Hz, 1H), 5.41 (d, J=9.7 Hz, 1H), 5.54 (ddd, J=9.8, 4.6, 2.7 Hz, 1H).

FABMS m/z 477 (M+H)+ $C_{26}H_{40}N_2O_4S$=476.

EXAMPLE 13

Compound 13

Compound 6 (15 mg, 0.036 mmol) was dissolved in dimethyl sulfoxide (1 ml), and a potassium phosphate buffer (10 mmol/L, pH=7.0, 0.5 ml) and 2-propanethiol (0.0067 ml, 0.072 mmol) were added thereto, followed by stirring at room temperature for 15 minutes. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was purified by silica gel column chromatography (2:3=hexane:ethyl acetate) to obtain Compound 13 (14 mg, 79%).

$^1$H NMR (300 MHz, CDCl$_3$) δ 0.81 (d, J=7.0 Hz, 3H), 1.0–2.1 (m, 10H), 1.18 (t, J=7.2 Hz, 3H), 1.21 (t, J=7.2 Hz, 3H), 1.26 (t, J=6.8 Hz, 3H), 1.32 (t, J=6.6 Hz, 3H), 2.5–2.7 (m, 2H), 2.89 (m, 1H), 3.1–3.8 (m, 9H), 3.74 (d, J=9.5 Hz, 1H), 4.42 (s, 1H), 4.54 (d, J=9.5 Hz, 1H), 5.40 (d, J=9.5 Hz, 1H), 5.55 (ddd, J=9.7, 4.5, 2.7 Hz, 1H).

FABMS m/z 491 (M+H)$^+$ C$_{27}$H$_{42}$N$_2$O$_4$S=490.

EXAMPLE 14

Compound 14

Compound 6 (15 mg, 0.036 mmol) was dissolved in dimethyl sulfoxide (1 ml), and a potassium phosphate buffer (10 mmol/L, pH=7.0, 0.5 ml) and thiophenol (0.0074 ml, 0.072 mmol) were added thereto, followed by stirring at room temperature for 35 minutes. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was purified by preparative thin layer chromatography (1:2=hexane:ethyl acetate) to obtain Compound 14 (12 mg, 64%).

$^1$H NMR (300 MHz, CDCl$_3$) δ 0.83 (t, J=7.2 Hz, 3H), 0.84 (d, J=7.0 Hz, 3H), 1.0–2.2 (m, 10H), 1.04 (t, J=7.2 Hz, 3H), 2.5–3.4 (m, 9H), 3.62 (dd, J=11.2, 5.7 Hz, 1H), 3.73 (m, 1H), 3.91 (d, J=9.9 Hz, 1H), 4.35 (s, 1H), 4.83 (d, J=9.9 Hz, 1H), 5.42 (d, J=9.9 Hz, 1H), 5.56 (ddd, J=9.9, 4.4, 2.6 Hz, 1H), 7.3–7.4 (m, 3H), 7.6–7.7 (m, 2H).

FABMS m/z 525 (M+H)$^+$ C$_{30}$H$_{40}$N$_2$O$_4$S=524.

EXAMPLE 15

Compound 15

Compound 6 (18 mg, 0.043 mmol) was dissolved in ethanol (3 ml), and hydroxylamine hydrochloride (30 mg, 0.43 mmol) and pyridine (36 ml) were added thereto, followed by stirring at room temperature for 30 minutes. An aqueous citric acid solution was added to the reaction mixture, and the mixture was extracted with ether. The organic layer was washed with saturated brine and then dried over anhydrous sodium sulfate. The solvent was evaporated under a reduced pressure, and the resulting residue was triturated with hexane to obtain Compound 15 (7.0 mg, 34%).

$^1$H NMR (300 MHz, CDCl$_3$) δ 0.76 (d, J=7.0 Hz, 3H), 0.9–2.0 (m, 10H), 1.16 (t, J=7.0 Hz, 3H), 1.20 (t, J=7.2 Hz, 3H), 2.1–2.7 (m, 3H), 3.1–3.9 (m, 9H), 4.26 (d, J=9.4 Hz, 1H), 5.41 (d, J=9.7 Hz, 1H), 5.5–5.6 (m, 1H).

FABMS m/z 448 (M+H)$^+$ C$_{24}$H$_{37}$N$_3$O$_5$=447.

EXAMPLE 16

Compounds 16 and 17

UCS 1025A (40 mg, 0.11 mmol) was dissolved in toluene (8 ml), and p-toluenesulfonic acid (4.0 mg, 0.021 mmol) was added thereto, followed by heating under reflux for 1 hour. The reaction mixture was cooled to room temperature, an aqueous sodium bicarbonate solution was added thereto, and the mixture was extracted with ethyl acetate. The organic layer was washed with saturated brine and then dried over anhydrous sodium sulfate. The solvent was evaporated under a reduced pressure, and the resulting residue was purified by silica gel column chromatography (9:1= hexane:ethyl acetate) to obtain Compound 16 (51 mg, 15%). The aqueous layer obtained above was adjusted to pH 7 by adding 1 mol/L hydrochloric acid and extracted with ethyl acetate. The organic layer was washed with saturated brine and dried over anhydrous sodium sulfate and then the solvent was evaporated under a reduced pressure to obtain Compound 17 (246 mg, 65%).

Compound 16 (Enol Form):

$^1$H NMR (300 MHz, CDCl$_3$) δ 1.06 (d, J=7.0 Hz, 3H), 1.1–2.0 (m, 10H), 2.46 (m, 1H), 2.53 (dd, J=11.0, 5.9 Hz, 1H), 3.51 (s, 2H), 5.43 (d, J=9.7 Hz, 1H), 5.5–5.6 (m, 1H), 6.00 (m, 1H), 6.44 (t, J=3.1 Hz, 1H), 7.10 (d, J=2.9 Hz, 1H), 11.6 (br S, 1H).

FABMS m/z 298 (M+H)$^+$ C$_{19}$H$_{23}$NO$_2$=297.

Compound 17 (Enol Form):

$^1$H NMR (300 MHz, CDCl$_3$) δ 0.8–2.0 (m, 10H), 1.06 (d, J=7.0 Hz, 3H), 2.47 (m, 1H), 2.59 (dd, J=11.2, 5.9 Hz, 1H), 3.79 (s, 2H), 5.44 (d, J=9.5 Hz, 1H), 5.5–5.6 (m, 1H), 6.82 (d, J=2.8 Hz, 1H), 7.11 (d, J=3.1 Hz, 1H), 11.4 (br s, 1H).

FABMS m/z 342 (M+H)$^+$ C$_{20}$H$_{23}$NO$_4$=341.

EXAMPLE 17

Compound 18

Compound 17 (6.7 mg, 0.020 mmol) was dissolved in methanol (2 ml), one drop of sulfuric acid was added thereto, followed by heating under reflux for 5 hours. The reaction mixture was cooled to room temperature, an aqueous sodium bicarbonate solution was added thereto, and the mixture was extracted with ethyl acetate. The organic layer was washed with water and saturated brine and then dried over anhydrous sodium sulfate. The solvent was evaporated under a reduced pressure to obtain Compound 18 (6.9 mg, 97%).

$^1$H NMR (300 MHz, CDCl$_3$) δ 1.0–2.0 (m, 1H), 1.06 (d, J=7.2 Hz, 3H), 2.48 (m, 1H), 2.60 (dd, J=11.2, 5.9 Hz, 1H), 3.85 (s, 5H), 5.45 (d, J=9.9 Hz, 1H), 5.58 (ddd, J=9.9, 4.4, 2.6 Hz, 1H), 6.79 (d, J=3.3 Hz, 1H), 7.08 (d, J=3.3 Hz, 1H), 11.4 (br s, 1H).

FABMS m/z 356 (M+H)$^+$ C$_{21}$H$_{25}$NO$_4$=355.

EXAMPLE 18

Compound 19

Compound 17 (30 mg, 0.088 mmol) was dissolved in dichloromethane (7 ml), and 2-chloro-1-methylpyridinium iodide (111 mg, 0.44 mmol) was added thereto, followed by stirring at room temperature for 20 minutes. Then, diethylamine (0.045 ml, 0.44 mmol) was added thereto, followed by stirring at room temperature for 10 minutes. Water was added to the reaction mixture, and the mixture was extracted with ethyl acetate. The organic layer was washed with saturated brine and then dried over anhydrous sodium sulfate. The solvent was evaporated under a reduced pressure, and the resulting residue was purified by silica gel column chromatography (2:1=hexane:ethyl acetate) to obtain Compound 19 (29 mg, 83%).

$^1$H NMR (300 MHz, CDCl$_3$) δ 1.0–2.0 (m, 10H), 1.04 (d, J=7.2 Hz, 3H), 1.24 (t, J=7.0 Hz, 6H), 2.45 (m, 1H), 2.59 (dd, J=11.2, 5.9 Hz, 1H), 3.52 (q, J=7.0 Hz, 4H), 3.75 (s, 2H), 5.41 (d, J=10.1 Hz, 1H), 5.5–5.6 (m, 1H), 6.52 (d, J=3.3 Hz, 1H), 7.08 (d, J=3.1 Hz, 1H), 11.3 (br s, 1H).

FABMS m/z 397 (M+H)$^+$ C$_{24}$H$_{32}$N$_2$O$_3$=396.

EXAMPLE 19

Compound 20

Compound 17 (10 mg, 0.029 mmol) was dissolved in tetrahydrofuran (3 ml), and N-bromosuccinimide (6.0 mg, 0.035 mmol) was added thereto, followed by stirring at room temperature for 10 minutes. Water was added to the reaction mixture, and the mixture was extracted with ethyl acetate. The organic layer was washed with saturated brine and dried over anhydrous sodium sulfate. The solvent was evaporated under a reduced pressure to obtain Compound 20 (12 mg, 99%).

$^1$H NMR (300 MHz, CDCl$_3$) δ 0.72 (d, J=7.2 Hz, 1.5H), 0.8–1.9 (m, 10H), 0.91 (t, J=7.2 Hz, 1.5H), 2.60 (m, 0.5H), 2.88 (m, 0.5H), 3.57 (d, J=19.3 Hz, 0.5H), 3.65 (d, J=19.4 Hz, 0.5H), 3.70 (dd, J=11.8, 5.8 Hz, 0.5H), 3.74 (dd, J=11.5, 5.8 Hz, 0.5H), 4.37 (d, J=19.4 Hz, 0.5H), 4.56 (d, J=19.3 Hz, 0.5H), 5.42 (d, J=9.9 Hz, 1H), 5.5–5.6 (m, 1H), 6.91 (d, J=3.3 Hz, 1H), 7.06 (d, J=3.5 Hz, 0.5H), 7.09 (d, J=3.3 Hz, 0.5H).

FABMS m/z 422, 420 (M+H)$^+$ C$_{20}$H$_{22}$$^{79}$BrNO$_4$=419.

EXAMPLE 20

Compound 21

Compound 20 (12 mg, 0.029 mmol) was dissolved in tetrahydrofuran (3 ml), and 1,8-diazabicyclo[5.4.0]-7-undecene (0.0095 ml, 0.064 mmol) was added thereto, followed by stirring at room temperature for 1 hour. Water was added to the reaction mixture, and the mixture was extracted with ethyl acetate. The organic layer was washed with saturated brine and dried over anhydrous sodium sulfate. The solvent was evaporated under a reduced pressure, and the resulting residue was purified by preparative thin layer chromatography (9:1=chloroform:methanol) to obtain Compound 21 (6.1 mg, 62%).

$^1$H NMR (300 MHz, CDCl$_3$) δ 0.82 (d, J=7.0 Hz, 3H), 1.0–2.0 (m, 10H), 2.60 (m, 1H), 3.50 (m, 1H), 5.43 (d, J=9.7 Hz, 1H), 5.56 (m, 1H), 6.56 (br s, 1H), 7.00 (br s, 1H), 8.14 (s, 1H).

FABMS m/z 340 (M+H)$^+$ C$_{20}$H$_{21}$NO$_4$=339.

EXAMPLE 21

Compound 22

Compound 18 (20 mg, 0.056 mmol) was dissolved in tetrahydrofuran (4 ml), and N-bromosuccinimide (11 mg, 0.062 mmol) was added thereto, followed by stirring at room temperature for 10 minutes. Water was added to the reaction mixture, and the mixture was extracted with ethyl acetate. The organic layer was washed with saturated brine and dried over anhydrous sodium sulfate. The solvent was evaporated under a reduced pressure to obtain a brominated product of Compound 18 (23 mg, 95%).

The brominated product of compound 18 (23 mg, 0.053 mmol) obtained above was dissolved in tetrahydrofuran (4 ml), and 1,8-diazabicyclo[5.4.0]-7-undecene (0.013 ml, 0.085 mmol) was added thereto, followed by stirring at room temperature for 20 minutes. Water was added thereto, and the mixture was extracted with ethyl acetate. The organic layer was washed with water and saturated brine and then dried over anhydrous sodium sulfate. The solvent was evaporated under a reduced pressure, and the resulting residue was purified by silica gel column chromatography (6:1=hexane:ethyl acetate) to obtain Compound 22 (10 mg, 53%).

$^1$H NMR (300 MHz, CDCl$_3$) δ 0.82 (d, J=7.2 Hz, 3H), 0.9–2.0 (m, 10H), 2.59 (m, 1H), 3.51 (dd, J=11.2, 5.9 Hz, 1H), 3.88 (s, 3H), 5.43 (d, J=9.7 Hz, 1H), 5.57 (ddd, J=9.7, 4.4, 2.4 Hz, 1H), 6.53 (d, J=3.3 Hz, 1H), 6.98 (d, J=3.1 Hz, 1H), 8.11 (S, 1H).

FABMS m/z 354 (M+H)$^+$ C$_{21}$H$_{23}$NO$_4$=353.

EXAMPLE 22

Compound 23

Compound 19 (29 mg, 0.073 mol) was dissolved in tetrahydrofuran (4 ml), and N-bromosuccinimide (16 mg, 0.088 mmol) was added thereto, followed by stirring at room temperature for 10 minutes. Water was added to the reaction mixture, and the mixture was extracted with ethyl acetate. The organic layer was washed with saturated brine and dried over anhydrous sodium sulfate. The solvent was evaporated under a reduced pressure, and the resulting residue was purified by preparative thin layer chromatography (2:1=hexane:ethyl acetate) to obtain a brominated product of Compound 19 (20 mg, 58%).

The brominated product of Compound 19 (20 mg, 0.056 mmol) obtained above was dissolved in tetrahydrofuran (4 ml), and 1,8-diazabicyclo[5.4.0]-7-undecene (0.010 ml, 0.067 mmol) was added thereto, followed by stirring at room temperature for 30 minutes. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was purified by silica gel column chromatography (4:1=hexane:ethyl acetate) to obtain Compound 23 (8.7 mg, 53%).

$^1$H NMR (300 MHz, CDCl$_3$) δ 0.81 (d, J=7.2 Hz, 3H), 1.0–2.0 (m, 10H), 1.22 (t, J=7.2 Hz, 6H), 2.58 (m, 1H), 3.4–3.6 (m, 5H), 5.41 (d, J=9.9 Hz, 1H), 5.56 (ddd, J=9.7, 4.4, 2.6 Hz, 1H), 6.22 (d, J=3.1 Hz, 1H), 7.00 (d, J=3.1 Hz, 1H), 8.02 (s, 1H).

FABMS m/z 395 (M+H)C$_{24}$H$_{30}$N$_2$O$_3$=394.

EXAMPLE 23

Compound 24

Compound 1 (20 mg, 0.054 mmol) was dissolved in dichloromethane (4 ml), and acetic anhydride (0.025 ml, 0.27 mmol) and 4-dimethylaminopyridine (1.3 mg, 0.011 mmol) were added thereto, followed by stirring at room temperature for 35 minutes. Water was added to the reaction mixture, and the mixture was extracted with ethyl acetate. The organic layer was washed with saturated brine and dried over anhydrous sodium sulfate. The solvent was evaporated under a reduced pressure, and the resulting residue was purified by preparative thin layer chromatography (3:2=hexane:ethyl acetate) to obtain Compound 24 (15 mg, 78%).

$^1$H NMR (300 MHz, CDCl$_3$) δ 0.79 (d, J=7.2 Hz, 3H), 1.0–2.0 (m, 10H), 2.65 (m, 1H), 3.34 (t, J=7.5 Hz, 2H), 3.77 (dd, J=11.2, 5.7 Hz, 1H), 3.85 (s, 3H), 3.88 (t, J=7.5 Hz, 2H), 5.41 (d, J=9.9 Hz, 1H), 5.56 (ddd, J=9.7, 4.6, 2.6 Hz, 1H), 7.86 (s, 1H).

FABMS m/z 356 (M+H)$^+$ C$_{21}$H$_{25}$NO$_4$=355.

EXAMPLE 24

Compound 25

Compound 6 (15 mg, 0.036 mmol) was dissolved in dichloromethane (4 ml), and acetic anhydride (0.017 ml, 0.18 mmol) and 4-dimethylaminopyridine (1.0 mg, 0.0082 mmol) were added thereto, followed by stirring at room temperature for 1 hour. Water was added to the reaction mixture, and the mixture was extracted with ethyl acetate. The organic layer was washed with saturated brine and dried over anhydrous sodium sulfate. The solvent was evaporated under a reduced pressure, and the resulting residue was purified by preparative thin layer chromatography (ethyl acetate) to obtain Compound 25 (10 mg, 70%).

$^1$H NMR (300 MHz, CDCl$_3$) δ 0.77 (d, J=7.2 Hz, 3H), 1.0–2.0 (m, 10H), 1.21 (t, J=7.1 Hz, 6H), 2.68 (m, 1H), 3.4–3.5 (m, 6H), 3.84 (dd, J=11.2, 5.7 Hz, 1H), 3.90 (t, J=7.4 Hz, 2H), 5.40 (d, J=9.7 Hz, 1H), 5.56 (m, 1H), 7.57 (s, 1H).

FABMS m/z 397 (M+H)$^+$ C$_{24}$H$_{32}$N$_2$O$_3$=396.

EXAMPLE 25

Compound 26

Compound 3 (10 mg, 0.028 mmol) was dissolved in dimethyl sulfoxide (1 ml), and ethanethiol (0.024 ml, 0.34 mmol) and triethylamine (0.0040 ml, 0.028 mmol) were added thereto, followed by stirring at room temperature for 1 hour. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was triturated with hexane to obtain Compound 26 (4.9 mg, 42%).

$^1$H NMR (300 MHz, CDCl$_3$) δ 0.75 (d, J=7.0 Hz, 3H), 0.9–2.1 (m, 10H), 1.14 (t, J=7.4 Hz, 3H), 2.4–2.7 (m, 5H), 2.81 (br d, J=5.9 Hz, 1H), 3.07 (m, 1H), 3.28 (dd, J=13.6, 5.7 Hz, 1H), 3.43 (m, 1H), 4.07 (d, J=10.6 Hz, 1H), 4.22 (d, J=10.5 Hz, 1H), 5.38 (d, J=9.7 Hz, 1H), 5.59 (ddd, J=9.7, 4.2, 2.2 Hz, 1H), 6.02 (s, 1H), 7.12 (br s, 1H), 7.62 (br s, 1H).

FABMS m/z 421 (M+H)$^+$ C$_{22}$H$_{32}$N$_2$O$_4$S 420.

EXAMPLE 26

Compound 27

Compound 6 (21 mg, 0.050 mmol) was dissolved in dichloromethane (2 ml), and methanol (1 ml) and trifluoroacetic acid (0.004 ml, 0.05 mmol) were added thereto, followed by stirring at room temperature for 23 hours. The reaction mixture was evaporated under a reduced pressure and the resulting residue was purified by preparative thin layer chromatography (9:1=chloroform:acetonitrile) to obtain Compound 27 (11 mg, 48%).

$^1$H NMR (400 MHz, CDCl$_3$) δ 0.79 (d, J=7.2 Hz, 3H), 0.9–1.9 (m, 10H), 1.22 (t, J=7.2 Hz, 3H), 1.23 (t, J=7.2 Hz, 3H), 2.2–2.4 (m, 2H), 2.60 (m, 1H), 3.0–3.3 (m, 3H), 3.30 (dd, J=7.2, 3.3 Hz, 1H), 3.35 (s, 3H), 3.39 (S, 3H), 3.56 (dd, J=11.2, 5.7 Hz, 1H), 3.62 (m, 2H), 3.8–3.9 (m, 2H), 4.56 (d, J=8.4 Hz, 1H), 5.41 (d, J=9.7 Hz, 1H), 5.56 (ddd, J=9.7, 4.6, 2.6 Hz, 1H).

FABMS m/z 461 (M+H)$^+$ C$_{26}$H$_{40}$N$_2$O$_5$=460.

EXAMPLE 27

Compounds 28 and 29

UCS 1025A (54 mg, 0.15 mmol) was dissolved in dichloromethane (8 ml), and m-chloroperbenzoic acid (50%, 156 mg, 0.45 mmol) was added thereto, followed by stirring at room temperature for 5 hours. A 10% aqueous sodium hydrogen sulfite solution was added to the reaction mixture, and the mixture was extracted with chloroform. The organic layer was washed with an aqueous sodium bicarbonate solution, water and saturated brine and then dried over anhydrous sodium sulfate. The solvent was evaporated under a reduced pressure, and the resulting residue was purified by preparative thin layer chromatography (9:1=chloroform:methanol) to obtain Compound 28 (22 mg, 38%) and Compound 29 (14 mg, 24%).

Compound 28:

$^1$H NMR (500 MHz, CDCl$_3$) δ 0.88 (d, J=7.1 Hz, 3H), 1.0–1.9 (m, 10H), 2.64 (m, 1H), 2.78 (m, 1H), 2.86 (m, 1H), 2.95 (dd, J=10.9, 6.5 Hz, 1H), 3.02 (d, J=4.1 Hz, 1H), 3.18 (dd, J=5.2, 4.0 Hz, 1H), 3.21 (dd, J=8.9, 1.4 Hz, 1H), 3.45 (ddd, J=12.0, 10.0, 4.4 Hz, 1H), 3.72 (br s, 1H), 3.82 (ddd, J=12.0, 9.1, 6.6 Hz, 1H), 4.34 (s, 1H), 5.13 (br s, 1H).

FABMS m/z 392 (M+H)$^+$ C$_{20}$H$_{25}$NO$_7$=391.

Compound 29:

$^1$H NMR (500 MHz, CDCl$_3$) δ 0.98 (d, J=7.2 Hz, 3H), 1.0–1.9 (m, 10H), 2.63 (m, 1H), 2.75 (m, 1H), 2.78 (m, 1H), 3.01 (dd, J=3.7, 1.4 Hz, 1H), 3.05 (m, 1H), 3.11 (dd, J=10.9, 4.4 Hz, 1H), 3.19 (dd, J=9.0, 1.8 Hz, 1H), 3.44 (ddd, J=11.9, 9.8, 4.9 Hz, 1H), 3.74 (br s, 1H), 3.89 (m, 1H), 4.36 (s, 1H), 5.11 (br s, 1H).

FABMS m/z 392 (M+H)$^+$ C$_{20}$H$_{25}$NO$_7$=391.

EXAMPLE 28

Compound 30

In an argon atmosphere, UCS 1025B (15 mg, 0.040 mmol) was dissolved in dimethylformamide (2 ml), followed by ice-cooling. Iodomethane (0.025 ml, 0.40 mmol) and sodium hydride (4.0 mg, 0.10 mmol) were added thereto, followed by stirring for 1 hour. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was purified by silica gel column chromatography (2:1=hexane:ethyl acetate) to obtain Compound 30 (9.4 mg, 58%).

$^1$H NMR (300 MHz, CDCl$_3$) δ 0.94 (d, J=7.0 Hz, 3H), 1.1–1.9 (m, 10H), 2.3–2.7 (m, 3H), 3.2–3.4 (m, 3H), 3.39 (5, 3H), 3.52 (s, 3H), 4.16 (ddd, J=12.1, 9.2, 3.5 Hz, 1H), 4.71 (S, 1H), 5.37 (d, J=9.7 Hz, 1H), 5.60 (ddd, J=9.7, 5.0, 2.4 Hz, 1H).

FABMS m/z 404 (M+H)$^+$ C$_{22}$H$_{29}$NO$_6$=403.

EXAMPLE 29

Compound 31

UCS 1025A (20 mg, 0.056 mmol) was dissolved in dichloromethane (5 ml), and acetic anhydride (0.026 ml, 0.28 mmol) and 4-dimethylaminopyridine (2.0 mg, 0.017 mmol) were added thereto, followed by stirring at room temperature for 20 minutes. Water was added to the reaction mixture, and the mixture was extracted with ethyl acetate. The organic layer was washed with saturated brine and dried over anhydrous sodium sulfate. The solvent was evaporated under a reduced pressure, and the resulting residue was purified by silica gel column chromatography (3:1= hexane:ethyl acetate) to obtain Compound 31 (15 mg, 67%).

$^1$H NMR (300 MHz, CDCl$_3$) δ 1.00 (d, J=6.8 Hz, 3H), 1.0–2.0 (m, 10H), 2.14 (s, 3H), 2.3–2.8 (m, 3H), 3.2–3.7 (m, 3H), 3.97 (m, 1H), 5.39 (d, J=9.9 Hz, 1H), 5.50 (s, 1H), 5.5–5.6 (m, 1H), 11.8 (br s, 1H).

FABMS m/z 402 (M+H)$^+$ C$_{22}$H$_{27}$NO$_6$=401.

EXAMPLE 30

Compound 32

UCS 1025A (200 mg, 0.557 mmol) was dissolved in tetrahydrofuran (10 ml), and N-bromosuccinimide (100 mg, 0.562 mmol) was added thereto, followed by stirring at room temperature for 15 minutes. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was recrystallized from ethyl acetate to obtain Compound 32 (155 mg, 64%).

$^1$H NMR (400 MHz, CDCl$_3$) δ 0.8–1.1 (m, 2H), 0.95 (d, J=7.1 Hz, 3H), 1.2–1.3 (m, 2H), 1.5–1.9 (m, 6H), 2.54 (m, 1H), 2.68 (m, 1H), 2.88 (m, 1H), 3.20 (dd, J=9.0, 1.7 Hz, 1H), 3.44 (ddd, J=12.0, 9.8, 4.9 Hz, 1H), 3.70 (dd, J=11.2, 5.4 Hz, 1H), 3.87 (ddd, J=12.2, 9.5, 6.1 Hz, 1H), 5.21 (s, 1H), 5.39 (d, J=10.0 Hz, 1H), 5.57 (ddd, J=9.8, 4.9, 2.7 Hz, 1H).

FABMS m/z 440, 438 (M+H)$^+$ C$_{20}$H$_{24}$$^{79}$BrNO$_5$=437.

EXAMPLE 31

Compound 33

Compound 32 (33 mg, 0.075 mmol) was dissolved in toluene (10 ml), and diethylamine (0.078 ml, 0.75 mmol) was added thereto, followed by heating under reflux for 80 minutes. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was purified by preparative thin layer chromatography (9:1= chloroform:methanol) to obtain Compound 33 (25 mg, 76%).

$^1$H NMR (400 MHz, CDCl$_3$) δ 0.76 (d, J=7.1 Hz, 3H), 1.0–1.9 (m, 10H), 2.4–2.6 (m, 2H), 2.69 (m, 1H), 3.36 (dd, J=9.3, 2.2 Hz, 1H), 3.40 (m, 1H), 3.95 (m, 1H), 4.05 (dd, J=11.2, 5.5 Hz, 1H), 4.48 (br s, 1H), 5.06 (s, 1H), 5.39 (d, J=9.8 Hz, 1H), 5.50 (ddd, J=9.8, 4.6, 2.6 Hz, 1H).

FABMS m/z 440, 438 (M+H)$^+$ C$_{20}$H$_{24}$$^{79}$BrNO$_5$=437.

EXAMPLE 32

Compound 34

Compound 32 (10 mg, 0.023 mmol) was suspended in methanol (2 ml), and potassium carbonate (6.3 mg, 0.046 mmol) was added thereto, followed by stirring at room temperature for 20 minutes. A 0.1 mol/L aqueous citric acid solution was added to the reaction mixture, and the mixture was extracted with ethyl acetate. The organic layer was washed with water and saturated brine and then dried over anhydrous sodium sulfate. The solvent was evaporated under a reduced pressure to obtain Compound 34 (9.0 mg, quantitative).

$^1$H NMR (400 MHz, CDCl$_3$) δ 0.67 (m, 1H), 0.91 (d, J=7.2 Hz, 3H), 1.0–1.9 (m, 9H), 2.3–2.5 (m, 2H), 2.68 (m, 1H), 2.81 (dd, J=11.2, 5.7 Hz, 1H), 3.19 (dd, J=7.2, 4.6 Hz, 1H), 3.31 (m, 1H), 3.64 (m, 1H), 3.79 (s, 3H), 4.11 (s, 1H), 5.37 (d, J=9.7 Hz, 1H), 5.53 (ddd, J=9.7, 4.4, 2.4 Hz, 1H).

FABMS m/z 390 (M+H)$^+$ C$_{21}$H$_{27}$NO$_6$=389.

EXAMPLE 33

Compound 35

Compound 33 (20 mg, 0.046 mmol) was suspended in methanol (4 ml), and potassium carbonate (13 mg, 0.094 mmol) was added thereto, followed by stirring at room temperature for 30 minutes. Water was added to the reaction mixture, and the mixture was extracted with ethyl acetate. The organic layer was washed with water and saturated brine and then dried over anhydrous sodium sulfate. The solvent was evaporated under a reduced pressure to obtain Compound 35 (11 mg, 61%).

$^1$H NMR (400 MHz, CDCl$_3$) δ 0.85 (d, J=7.3 Hz, 3H), 0.9–1.8 (m, 10H), 2.38 (m, 1H), 2.64 (m, 1H), 2.88 (m, 1H), 3.16 (dd, J=7.6, 0.9 Hz, 1H), 3.23 (m, 1H), 3.42 (dd, J=11.3, 5.5 Hz, 1H), 3.71 (s, 3H), 3.74 (m, 1H), 4.17 (s, 1H), 5.39 (d, J=10.0 Hz, 1H), 5.57 (ddd, J=9.8, 4.6, 2.4 Hz, 1H).

FABMS m/z 390 (M+H)$^+$ C$_{21}$H$_{27}$NO$_6$=389.

EXAMPLE 34

Compound 36

Compound 32 (438 mg, 1.00 mmol) was suspended in allyl alcohol (15 ml), and potassium carbonate (276 mg, 2.00 mmol) was added thereto, followed by stirring at room temperature for 80 minutes. An aqueous ammonium chloride solution was added to the reaction mixture, and the mixture was extracted with ethyl acetate. The organic layer was washed with water and saturated brine and then dried over anhydrous sodium sulfate. The solvent was evaporated under a reduced pressure, and the resulting residue was purified by silica gel column chromatography (2:1= hexane:ethyl acetate) to obtain Compound 36 (188 mg, 45%).

$^1$H NMR (400 MHz, CDCl$_3$) δ 0.86 (m, 1H), 0.92 (d, J=7.2 Hz, 3H), 1.0–1.9 (m, 9H), 2.3–2.5 (m, 2H), 2.68 (m, 1H), 2.81 (dd, J=11.2, 5.8 Hz, 1H), 3.2–3.4 (m, 2H), 3.67 (m, 1H), 3.82 (m, 1H), 4.09 (s, 1H), 4.68 (m, 2H), 5.2–5.4 (m, 3H), 5.53 (ddd, J=9.7, 4.4, 2.6 Hz, 1H).

FABMS m/z 416 (M+H)$^+$ C$_{23}$H$_{21}$NO$_6$=415.

EXAMPLE 35

Compound 37

In an argon atmosphere, Compound 36 (176 mg, 0.424 mmol) was dissolved in tetrahydrofuran (10 ml), followed by ice-cooling. Pyrrolidine (0.106 ml, 1.3 mmol) and tetrakistriphenylphosphine palladium (25 mg, 0.021 mmol) were added thereto, followed by stirring at 0° C. for 4 hours. An aqueous ammonium chloride solution was added to the reaction mixture, and the mixture was extracted with ethyl acetate. The organic layer was washed with water and saturated brine and then dried over anhydrous sodium sulfate. The solvent was evaporated under a reduced pressure, and the resulting residue was purified by silica gel column chromatography (9:1=chloroform:methanol) to obtain Compound 37 (48 mg, 30%).

$^1$H NMR (400 MHz, CDCl$_3$) δ 0.7–3.8 (m, 20H), 4.21 (br s, 1H), 5.37 (d, J=9.9 Hz, 1H), 5.50 (s, 1H), 5.52 (m, 1H).

FABMS m/z 376 (M+H)$^+$ C$_{20}$H$_{25}$NO$_6$=375.

EXAMPLE 36

Compound 38

Compound 37 (20 mg, 0.053 mmol) was dissolved in dichloromethane (4 ml), and 2-chloro-1-methylpyridinium iodide (68 mg, 0.27 mmol) and diethylamine (0.028 ml, 0.27 mmol) were added thereto, followed by stirring at room temperature for 12 hours. Water was added to the reaction mixture, and the mixture was extracted with ethyl acetate. The organic layer was washed with water and saturated brine and then dried over anhydrous sodium sulfate. The solvent was evaporated under a reduced pressure, and the resulting residue was purified by silica gel column chromatography (19:1=chloroform:methanol) to obtain Compound 38 (19 mg, 83%).

$^1$H NMR (400 MHz, CDCl$_3$) δ 0.66 (m, 1H), 0.91 (d, J=7.2 Hz, 3H), 1.0–1.9 (m, 9H), 1.18 (t, J=7.1 Hz, 3H), 1.25 (t, J=7.1 Hz, 3H), 2.31 (m, 1H), 2.47 (m, 1H), 2.72 (m, 1H), 2.81 (dd, J=11.2, 5.7 Hz, 1H), 3.2–3.4 (m, 5H), 3.65 (m, 1H), 3.78 (m, 1H), 3.89 (s, 1H), 5.35 (d, J=9.7 Hz, 1H), 5.52 (ddd, J=9.7, 4.4, 2.6 Hz, 1H).

FABMS m/z 431 (M+H)$^+$ C$_{24}$H$_{34}$N$_2$O$_5$=430.

EXAMPLE 37

Compounds 39 and 40

UCS 1025A (4.8 mg, 0.013 mmol) was dissolved in methanol (1 ml) and then, under ice-cooling, excess diazomethane (an ether solution, 1 ml) was added thereto, and the mixture was allowed to stand for 30 minutes. The reaction mixture was concentrated and then the residue was purified by preparative thin layer chromatography (1:1= hexane:ethyl acetate) to obtain Compound 39 (1.3 mg, 24%) and Compound 40 (2.3 mg, 45%).

Compound 39:

$^1$H NMR (500 MHz, CDCl$_3$) δ 0.73 (td, J=12.0, 3.7 Hz, 1H), 0.86 (d, J=7.1 Hz, 3H), 1.0–1.9 (m, 9H), 2.42 (m, 1H), 2.64 (m, 1H), 2.68 (m, 1H), 3.13 (dd, J=11.2, 5.6 Hz, 1H), 3.18 (dd, J=7.6, 1.5 Hz, 1H), 3.33 (ddd, J=12.2, 9.5, 2.7 Hz, 1H), 3.77 (dd, J=8.3, 5.9 Hz, 1H), 3.81 (s, 3H), 4.21 (d, J=2.0 Hz, 1H), 5.37 (d, J=9.8 Hz, 1H), 5.55 (ddd, J=9.8, 4.6, 2.7 Hz, 1H), 6.70 (br s, 1H).

FABMS m/z 416 (M+H)$^+$ C$_{22}$H$_{29}$N$_3$O$_5$=415.

Compound 40:

$^1$H NMR (500 MHz, CDCl$_3$) δ 0.78 (d, J=7.1 Hz, 3H), 0.85. (m, 1H), 1.08 (m, 1H), 1.2–1.4 (m, 2H), 1.54 (m, 1H), 1.7–1.8 (m, 4H), 1.86 (m, 1H), 2.31 (s, 3H), 2.39 (s, 1H), 2.51 (ddd, J=13.2, 10.8, 2.1 Hz, 1H), 2.60 (m, 1H), 2.72 (ddt, J=13.2, 6.8, 9.3 Hz, 1H), 3.18 (d, J=6.8 Hz, 1H), 3.36 (ddd, J=10.8, 9.2, 2.1 Hz, 1H), 3.57 (s, 3H), 3.71 (dd, J=11.3, 5.7 Hz, 1H), 3.82 (td, J=10.8, 9.3 Hz, 1H), 5.37 (br d, J=9.8 Hz, 1H), 5.52 (ddd, J=9.8, 5.1, 2.6 Hz, 1H).

FABMS m/z 388 (M+H)$^+$ C$_{22}$H$_{29}$NO$_5$=387.

EXAMPLE 38

Compound 41

UCS 1025A (2.0 mg, 0.0056 mmol) was dissolved in a mixed solvent of Tris buffer (50 mmol/L, pH 8.0, 2.0 ml) and methanol (0.2 ml), followed by ice-cooling. An aqueous 2-mercaptoethanol solution (500 mmol/L, 0.020 ml) was added thereto, followed by stirring for 30 minutes. The mixture was acidified by adding a phosphate buffer (1.0 mol/L, pH 5.9, 0.2 ml) and then extracted with chloroform. The organic layer was dried over anhydrous sodium sulfate and concentrated under a reduced pressure, and the resulting residue was purified by silica gel column chromatography (100:1=ethyl acetate:acetic acid) to obtain Compound 41 (2.0 mg, 82%).

$^1$H NMR (400 MHz, CDCl$_3$) δ 0.81 (d, J=7.1 Hz, 3H), 0.9–1.9 (m, 10H), 2.42 (dd, J=13.3, 8.0 Hz, 1H), 2.56 (m, 1H), 2.6–2.8 (m, 2H), 2.97 (dt, J=14.5, 5.9 Hz, 1H), 3.04 (d, J=6.5 Hz, 1H), 3.34 (t, J=10.5 Hz, 1H), 3.47 (dd, J=11.3, 5.8 Hz, 1H), 3.68 (dt, J=10.5, 8.0 Hz, 1H), 3.89 (t, J=5.9 Hz, 2H), 3.92 (d, J=10.5 Hz, 1H), 4.43 (d, J=10.5 Hz, 1H), 5.40 (d, J=9.8 Hz, 1H), 5.54 (ddd, J=9.8, 4.5, 2.6 Hz, 1H).

FABMS m/z 436 (M–H)$^-$ C$_{22}$H$_{31}$NO$_6$S=437.

EXAMPLE 39

Compound 42

Compound 42 (2.0 mg, 79%) was obtained in a manner similar to that in Example 38 using 3-mercaptopropanol instead of 2-mercaptoethanol.

$^1$H NMR (400 MHz, CDCl$_3$) δ 0.82 (d, J=7.1 Hz, 3H), 0.95 (m, 1H), 1.0–2.0 (m, 11H), 2.42 (dd, J=12.0, 7.8 Hz, 1H), 2.5–2.9 (m, 4H), 3.01 (d, J=6.4 Hz, 1H), 3.32 (t, J=10.8 Hz, 1H), 3.43 (dd, J=11.2, 5.9 Hz, 1H), 3.73 (dt, J=10.8, 8.3 Hz, 1H), 3.75 (m, 1H), 3.80 (m, 1H), 3.84 (d, J=10.3 Hz, 1H), 4.35 (d, J=10.3 Hz, 1H), 5.41 (d, J=10.0 Hz, 1H), 5.55 (ddd, J=10.0, 4.6, 2.7 Hz, 1H).

EXAMPLE 40

Compound 43

Compound 43 (2.0 mg, 0.80%) was obtained in a manner similar to that in Example 38 using 1-propanethiol instead of 2-mercaptoethanol.

$^1$H NMR (500 MHz, CDCl$_3$) δ 0.81 (d, J=7.1 Hz, 3H), 0.93 (m, 1H), 0.99 (t, J=7.3H, 3H), 1.0–1.9 (m, 1H), 2.46 (dd, J=12.8, 7.8 Hz, 1H), 2.5–2.8 (m, 4H), 2.99 (d, J=6.9 Hz, 1H), 3.31 (t, J=11.0 Hz, 1H), 3.43 (dd, J=11.2, 5.8 Hz, 1H), 3.70 (dt, J=11.0, 8.6 Hz, 1H), 3.77 (d, J=9.7 Hz, 1H), 4.35 (d, J=9.7 Hz, 1H), 5.41 (d, J=9.8 Hz, 1H), 5.55 (ddd, J=9.8, 4.6, 2.7 Hz, 1H).

FABMS m/z 436 (M+H)$^+$ C$_{23}$H$_{33}$NO$_5$S=435.

EXAMPLE 41

Compound 44

UCS 1025B (38 mg, 0.10 mmol) was dissolved in methanol (3 ml), followed by ice-cooling. Sodium borohydride (9.0 mg, 0.22 mmol) was added thereto, followed by stirring at room temperature for 1 hour. Water was added to the reaction mixture, and the mixture was extracted twice with ethyl acetate. The organic layer was washed with saturated brine and dried over anhydrous sodium sulfate. The solvent was evaporated under a reduced pressure, and the resulting residue was purified by silica gel column chromatography (19:1=chloroform:methanol) to obtain Compound 44 (25 mg, 66%).

FABMS m/z 378 (M+H)$^+$ C$_{20}$H$_{27}$NO$_6$=377.

INDUSTRIAL APPLICABILITY

According to the present invention, novel UCS 1025 derivatives having antitumor activity or antibacterial activity can be provided.

What is claimed is:

1. A compound represented by formula (I):

(I)

wherein $R^1$ represents hydrogen, or lower alkyl, $NR^9R^{10}$, $SR^{12}$ or $OR^{13}$;

$R^2$ is hydrogen or is combined with $R^3$ to represent a bond;

$R^3$ represents hydrogen, $OR^{15}$ or halogen, or is combined with $R^2$ to represent a bond;

$R^4$ represents hydrogen, $CO_2R^{16}$ or $CONR^{17}R^{18}$;

$R^5$ represents hydrogen or is combined with $R^6$ to represent a bond;

$R^6$ represents hydrogen or $OR^{19}$, or is combined with $R^5$ to represent a bond;

$R^7$ represents hydrogen or is combined with $R^8$ to represent =O;

$R^8$ represents hydroxy or is combined with $R^7$ to represent =O;

$R^9$ and $R^{10}$ independently represent hydrogen, substituted or unsubstituted lower alkyl, substituted or unsubstituted lower alkenyl, substituted or unsubstituted lower alkynyl, substituted or unsubstituted aryl, substituted or unsubstituted aralkyl or $OR^{11}$, or $R^9$ and $R^{10}$ are combined together with the adjacent N to form a substituted or unsubstituted heterocyclic ring;

$R^{11}$ represents hydrogen or lower alkyl;

$R^{12}$ represents hydrogen, substituted or unsubstituted lower alkyl, substituted or unsubstituted lower alkenyl, substituted or unsubstituted lower alkynyl, substituted or unsubstituted aryl, or substituted or unsubstituted aralkyl;

$R^{13}$ represents hydrogen, substituted or unsubstituted lower alkyl, substituted or unsubstituted lower alkenyl, or substituted or unsubstituted lower alkynyl;

$R^{15}$ represents hydrogen, substituted or unsubstituted lower alkyl, substituted or unsubstituted lower alkenyl, substituted or unsubstituted lower alkynyl, substituted or unsubstituted aralkyl, or substituted or unsubstituted lower alkanoyl;

$R^{16}$ represents hydrogen, substituted or unsubstituted lower alkyl, substituted or unsubstituted lower alkenyl, substituted or unsubstituted lower alkynyl, substituted or unsubstituted aryl, or substituted or unsubstituted aralkyl;

$R^{17}$ and $R^{18}$ independently represent hydrogen, substituted or unsubstituted lower alkyl, substituted or unsubstituted lower alkenyl, substituted or unsubstituted lower alkynyl, substituted or unsubstituted aryl, or substituted or unsubstituted aralkyl, or $R^{17}$ and $R^{18}$ are combined together with the adjacent N to form a substituted or unsubstituted heterocyclic ring;

$R^{19}$ represents hydrogen, substituted or unsubstituted lower alkyl, substituted or unsubstituted lower alkenyl, substituted or unsubstituted lower alkynyl, substituted or unsubstituted aralkyl, or substituted or unsubstituted lower alkanoyl;

---- represents a single bond or a double bond; and a represents an oxygen atom or both carbon atoms to which a is bound are joined by a double bond, or a pharmaceutically acceptable salt thereof with the proviso that $R^1$ does not represent hydrogen when $R^2$ and $R^3$ are combined to represent a bond, $R^4$ represents carboxy, $R^5$ represents hydrogen, $R^6$ represents hydroxy, $R^7$ and $R^8$ are combined to represent =O, and ---- and a both represent a single bond.

2. The compound according to claim 1, wherein $R^1$ is hydrogen, $NR^9R^{10}$, $SR^{12}$ or $OR^{13}$, or a pharmaceutically acceptable salt thereof.

3. The compound according to claim 1 or 2, wherein $R^7$ and $R^8$ are combined to represent =O, or a pharmaceutically acceptable salt thereof.

4. The compound according to claim 3, wherein $R^4$ is hydrogen, or a pharmaceutically acceptable salt thereof.

5. A method for treating bacterial infection, comprising administrating the compound or the pharmaceutically acceptable salt thereof according to claim 1 or 2 to a patient in need thereof.

6. A method for treating a renal carcinoma, comprising administrating the compound or the pharmaceutically acceptable salt thereof according to claim 1 or 2 to a patient in need thereof.

7. A medicament comprising, as an active ingredient, the compound or the pharmaceutically acceptable salt thereof according to claim 1 or 2 and a pharmaceutically acceptable excipient.

8. The method according to claim 6, wherein the renal carcinoma is malignant.

9. A method of manufacturing an agent for treating renal carcinomas, comprising selecting the compound or the pharmaceutically acceptable salt thereof according to claim 1 or 2 and admixing said compound or salt with a pharmaceutically acceptable excipient.

10. The compound according to claim 1 or 2, wherein $R^2$ and $R^3$ are combined to represent a bond, or a pharmaceutically acceptable salt thereof.

11. The compound according to claim 10, wherein $R^7$ and $R^8$ are combined to represent =O, or a pharmaceutically acceptable salt thereof.

12. The compound according to claim 3, wherein $R^4$ is $CO_2R^{16}$, or a pharmaceutically acceptable salt thereof.

13. The compound according to claim 3, wherein $R^4$ is $CONR^{17}R^{18}$, or a pharmaceutically acceptable salt thereof.

* * * * *

UNITED STATES PATENT AND TRADEMARK OFFICE
CERTIFICATE OF CORRECTION

PATENT NO. : 6,869,971 B1
DATED : March 22, 2005
INVENTOR(S) : Tsutomu Akama et al.

It is certified that error appears in the above-identified patent and that said Letters Patent is hereby corrected as shown below:

<u>Title page,</u>
Item [30], Foreign Application Priority Data,
"11/298972" should read -- 11-298972 --.

<u>Column 6,</u>
Line 46, "include" should be deleted.

<u>Column 9,</u>
Line 46, "OC" should read -- 0° C --.

<u>Column 13,</u>
Line 47, "(In" should read -- (Im) --.

<u>Column 15,</u>
Line 52, "CONR$^{16}$" should read -- COOR$^{16}$ --.

<u>Column 16,</u>
Line 14, "R$^{3a}$" should read -- R$^{3e}$ --.

<u>Column 30,</u>
Line 40, "(S," (both occurrences) should read -- (s, --; and
Line 43, "(S," should read -- (s, --.

<u>Column 36,</u>
Line 19, "(S," should read -- (s, --.

<u>Column 38,</u>
Line 2, "(S," should read -- (s, --.

UNITED STATES PATENT AND TRADEMARK OFFICE
CERTIFICATE OF CORRECTION

PATENT NO. : 6,869,971 B1
DATED : March 22, 2005
INVENTOR(S) : Tsutomu Akama et al.

It is certified that error appears in the above-identified patent and that said Letters Patent is hereby corrected as shown below:

Column 43,
Line 14, "hydrogen, or" should read -- hydrogen, --.

Signed and Sealed this

Nineteenth Day of July, 2005

JON W. DUDAS
*Director of the United States Patent and Trademark Office*